US006928131B2

(12) United States Patent
Olshansky et al.

(10) Patent No.: US 6,928,131 B2
(45) Date of Patent: Aug. 9, 2005

(54) METHOD FOR DETECTING AN EXPLOSIVE IN AN OBJECT UNDER INVESTIGATION

(75) Inventors: Yury Iosiphovich Olshansky, Saint-Petersburg (RU); Sergey Galievich Philippov, Saint-Petersburg (RU); Nikolai Erikovich Gjibovski, Saint-Petersburg (RU)

(73) Assignee: Ratec, Ltd., St. Petersburg (RU)

( * ) Notice: Subject to any disclaimer, the term of this patent is extended or adjusted under 35 U.S.C. 154(b) by 0 days.

(21) Appl. No.: 10/221,819

(22) PCT Filed: Apr. 24, 2002

(86) PCT No.: PCT/RU02/00192

§ 371 (c)(1),
(2), (4) Date: Nov. 29, 2002

(87) PCT Pub. No.: WO03/040713

PCT Pub. Date: May 15, 2003

(65) Prior Publication Data

US 2003/0147484 A1 Aug. 7, 2003

(30) Foreign Application Priority Data

Nov. 8, 2001 (RU) .................................. 2001129804

(51) Int. Cl.$^7$ ................................................ G21G 1/06
(52) U.S. Cl. ..................... 376/158; 358/57; 358/53; 250/370.09; 250/390.01
(58) Field of Search ................... 376/157, 158, 376/166, 159; 250/370.09, 390.01, 390.04; 378/57, 53

(56) References Cited

U.S. PATENT DOCUMENTS 3,597,607 A * 8/1971 Campbell et al. ............ 250/307
4,862,004 A * 8/1989 Koike et al. ................. 250/369
4,918,315 A * 4/1990 Gomberg et al. ...... 250/390.04

(Continued)

FOREIGN PATENT DOCUMENTS

| EP | 0 297 249 | 3/1988 | ............ G01V/5/00 |
| EP | 0 295 429 | 5/1988 | ............ G01V/5/00 |
| EP | 0 336 634 | 3/1989 | ............ G01V/5/00 |
| RU | 2065156 | 8/1996 | |
| WO | WO 91/14938 | 10/1991 | ......... G01N/23/222 |
| WO | WO 9613839 A | * 5/1996 | |

*Primary Examiner*—Michael J. Carone
*Assistant Examiner*—R Palabrica
(74) *Attorney, Agent, or Firm*—Jeffrey Weiss; Harry M. Weiss; Weiss, Moy & Harris, P.C.

(57) ABSTRACT

A method for detecting an explosive in an object under investigation involves the initial X-ray irradiation of the object under investigation, e.g. a piece of luggage or mailing, and forming its X-ray images; using the X-ray images to detect areas with a high density of organic materials and identifying articles therein; determining the location, dimensions and supposed mass of an unidentified article; determining and forming a directional pattern of the neutron radiator corresponding to the dimensions of the unidentified article. The method further includes subsequent thermal neutron irradiation of the area with the unidentified article; recording gamma-ray quanta having the energy of 10.8 MeV and cascade gamma-ray quanta with energies of 5.534 and 5.266 MeV by at least two gamma-ray detectors; counting of simultaneously recorded pairs of cascade gamma-ray quanta; determination of the overall gamma-ray intensity, taking into account weight factors in readings of the detectors; determination of the threshold value for the overall gamma-ray intensity basing on the supposed mass of explosive being detected; and making a decision in the event the threshold value of overall gamma-ray intensity is exceeded. When checking small-size objects, the neutron irradiation step is preceded by replacing the ambient air by a gaseous medium not containing nitrogen.

12 Claims, 11 Drawing Sheets

U.S. PATENT DOCUMENTS

| | | | |
|---|---|---|---|
| 5,078,952 A | | 1/1992 | Gozani et al. ............... 376/159 |
| 5,080,856 A | * | 1/1992 | Grenier et al. .............. 376/159 |
| 5,114,662 A | | 5/1992 | Gozani et al. ............... 376/159 |
| 5,124,554 A | * | 6/1992 | Fowler et al. ............ 250/358.1 |
| 5,144,140 A | | 9/1992 | Allyson et al. ............. 250/358 |
| 5,153,439 A | | 10/1992 | Gozani et al. ............... 376/390 |
| 5,182,764 A | * | 1/1993 | Peschmann et al. .......... 378/57 |
| 5,200,626 A | | 4/1993 | Schultz et al. .............. 250/390 |
| 5,251,240 A | * | 10/1993 | Grodzins .................... 376/157 |
| 5,388,128 A | | 2/1995 | Gozani ....................... 376/159 |
| 5,420,905 A | * | 5/1995 | Bertozzi ...................... 378/88 |
| 5,905,806 A | * | 5/1999 | Eberhard et al. ........... 382/100 |
| 6,205,195 B1 | * | 3/2001 | Lanza ........................ 376/157 |
| 6,393,085 B1 | * | 5/2002 | Heller et al. ................ 376/158 |
| 6,438,189 B1 | * | 8/2002 | Vourvopoulos ............. 376/159 |

\* cited by examiner

METHOD FOR DETECTING AN EXPLOSIVE IN AN OBJECT UNDER INVESTIGATION

FIELD OF THE INVENTION

The present invention relates to the field of radiographic and neutron radiation analysis of materials and, specifically, to methods for detecting nitrogen-containing explosives present in various objects.

The present invention can be used by security services in fighting against terrorism and organized crime on passenger and freight transport, at public and post offices in order to detect explosives concealed in objects under inspection, first of all, in mailings, passengers' baggage and hand luggage without the opening and examination thereof.

PRIOR ART

Counteracting illegal circulation of explosives and terrorist acts performed with their used has become one of the main tasks in activities of security services of civilized countries in the fight against terrorism and organized crime. One of the lines of this counteraction is connected with organizing, whenever necessary, control at airports, governmental and diplomatic establishments, nuclear power stations, post offices over objects such as briefcases, bags, suitcases, luggage packages, electronic equipment, computers, mobile phones and the like, as well as mailings, since these objects are most frequently used by terrorists and criminals to conceal explosives when committing terrorist acts or illegally transporting explosives.

The necessity to control large flows of mailings or inspect hand luggage and baggage of passengers, primarily at airports, when checking and examination time is limited, requires using methods and equipment, which would not require opening and visually inspecting each object under investigation, but would ensure rapid detection of explosives with a high probability of correct detection and low number of false alarms.

Among numerous prior art methods of detecting explosives in objects under investigation the following three groups of methods have found practical use today.

The first group comprises various methods using X-rays to detect explosives. These methods involve the exposure of an object under investigation to X-rays with an energy of 100 to 150 keV, recording X-rays that have passed through the object under investigation and identification of an explosive on the basis of X-ray attenuation by materials contained in the object under investigation depending on the atomic numbers of chemical elements contained by said materials (Patrick Flanagan, "Technology vs. Terror", EUSA, 1989, No. 7, p.p. 46–49, 51; advertising brochures and datasheets of EG&G Astrophysics Research Corporation, Long-Beach, Calif., USA, and In Vision Technologies, Foster City, Calif., USA).

Since modern explosives, particularly plastic ones, predominantly consist of chemical elements of a low atomic number, they display only a weak absorption of 100–150 keV X-rays. This makes it difficult to effectively detect explosives made in unconventional configurations or masked by way of placing them, for instance, into bars of soap or electronic devices. The practice of applying detection methods based on the X-rays has shown that explosives can be found with their use in no more than 40–60% of cases.

Methods of the second group are based upon the fact that most explosives belong to the class of highly volatile organic compounds characterized by a high vapor pressure. These methods provide for the use of gas chromatography and ion mobility spectrometry in making a chemical analysis of vapors emitted by an explosive and/or particles thereof, which may be present on the surface of the object under investigation. By the results of this analysis a decision is made about the presence of an explosive in the object under investigation (Hughes D. Thermedics Begins Production of Bomb Detection Unit, Aviation Week & Space Technology, Jun. 19, 1989). Such method has been realized, for instance, in the explosive and drug detection system IONSCAN 350 produced by Barringer Instruments, Ltd., Canada (Intersec. The Journal of International Security, Vol. 3, No. 6, November 1993).

Technical means implementing the aforementioned methods have a high sensitivity, but are incapable of detecting most powerful plastic explosives due to their very low vapor pressure. Moreover, these methods do not guarantee detecting all types of explosives if the latter are placed in a fluid-tight packing or specially treated packing.

Explosive detection methods belonging to the third group are based on the determination of the presence and concentration of major chemical elements present in the explosive composition by means of a neutron radiation analysis. The prior art explosive detection methods of this kind and units implementing thereof (U.S. Pat. No. 5,114,662, 1992; U.S. Pat. No. 5,144,140, 1992; U.S. Pat. No. 5,388,128, 1995; EP 0295429, 1992; EP 0297249, 1993) comprise steps of positioning of an object under investigation into a radiation-protected chamber; exposing it to thermal neutrons; recording the secondary gamma radiation of 10.8 MeV energy; finding, on the basis of the results of secondary gamma radiation recording, the distribution of nitrogen concentration within the object under investigation and determining the presence of an explosive in said object by the finding an increased nitrogen concentration.

All modern explosives are known to contain a fairly large quantity of nitrogen corresponding to 9 to 35 mass percent when density of an explosive is in the range 1.25 to 2.00 $g/cm^3$. The thermal neutron irradiation of an explosive at about 0.025 eV brings about a radiation capture of thermal neutrons by nuclei of nitrogen-14 atoms, which results in the formation of a nucleus of nitrogen-15 atoms in exited state. During the transition from the exited state to the ground state about 14% of nuclei of nitrogen-15 atoms on average emit gamma-ray quanta of 10.8 MeV.

However, during radiation capture of thermal neutrons not only explosives emit 10.8 MeV gamma-ray quanta, but also all other nitrogen-containing materials present in the object under investigation, such as wool, leather, nylon, silk, as well as the air filling and surrounding the object under investigation. Compared with explosives, most non-explosive nitrogen-containing materials have a considerably larger volume, the nitrogen content being about equal for all such materials. This is why the information about the distribution of nitrogen concentration within an object under investigation allows to distinguish an explosive with a high nitrogen concentration from other nitrogen-containing materials that do not belong to explosives.

At the same time, the aforementioned prior art methods make it possible to obtain only a rather approximate distribution of nitrogen concentration within an object under investigation for the reason that each gamma-ray detector registers gamma-ray quanta emitted from the entire volume of the object under investigation being exposed to thermal neutrons, including gamma-ray quanta from the nitrogen of ambient air also exposed to thermal neutrons. Furthermore, while an object under investigation is continuously transported by the conveyor through the radiation-protected chamber, the recorded number of gamma-ray quanta may be determined by their emission from all nitrogen-containing materials exposed, including non-explosives distributed along the length of the object under investigation. First, this hampers locating the explosive in the object under investigation and, second, it increases the probability of false alarms. Moreover, thresholds levels in detection of explosives by said prior art methods appears to be inadmissibly high since, on the average, only about 14% of nuclei of nitrogen atoms contained in the explosive emit the above described gamma radiation.

All explosives are known to have not only a high nitrogen density, but high oxygen density as well, said value lying for major types of explosives within the range of 0.80 to 1.15 g/cm$^3$. Practically all known materials that are not explosive, but cause false alarms due to the high nitrogen density, e.g. nylon, silk, wool, leather, melamine, etc., have a low oxygen density. In this connection, an attempt has been made to use the ongoing nuclear interactions, for instance, between fast neutrons of 14 MeV energy and oxygen nuclei, in order to detect secondary gamma radiation of 6.1 MeV and thus to obtain additional information about oxygen density in an object under investigation. By combining the obtained results on intensity of secondary gamma radiation from nitrogen and oxygen it becomes possible to make an assessment of the presence or absence of an explosive in the object under investigation.

Therefore, a number of other prior art explosive detection methods based on the neutron radiation analysis of materials and units for their implementation (U.S. Pat. No. 5,080,856, 1992; U.S. Pat. No. 5,200,626, 1993) provide for positioning an object under investigation in the radiation-protected chamber; simultaneously exposing the object under investigation to thermal neutrons at 0.025 eV and fast neutrons at about 14 MeV produced with the use of controlled pulsed sources of fast neutrons; recording the instantaneous rates of 10.8 MeV gamma radiation emitted due to the radiation capture of thermal neutrons by nuclei of nitrogen-14 atoms, and 6.1 MeV gamma radiation emitted by nuclei of oxygen-16 atoms in exited state resulting from the interaction between fast neutrons at around 14 MeV and stable nuclei of oxygen-16 atoms; using the results of said gamma radiation recording to obtain information on the concentration of nitrogen and oxygen in the object under investigation; and making a decision on the presence of an explosive in said object by finding an increased concentration of nitrogen and oxygen and a value of the nitrogen/oxygen ratio lying in a predetermined range.

An additional recording 6.1 MeV gamma radiation increases information content of the method and, consequently, a probability of correct explosive detection inherent to said method. However, recording gamma rays of said quantum energy without cutting off the pulsed source of fast neutrons is complicated due to the presence of gamma radiation having quantum energies within the range of 5 to 7 MeV emitted during nuclear interactions of thermal and fast neutrons with nuclei of atoms of a number of other chemical elements, such as chlorine, manganese, sodium or iron, since this makes it necessary to use detectors of a very high resolution. This disadvantage is eliminated by the disconnection of the controlled pulsed source of fast neutrons or removal of the object under investigation from the radiation-protected chamber for a time commensurable to the oxygen-16 halftime. Such measures however lead to a longer overall screening time and require a greater sophistication in the design of units realizing prior art methods of the discussed type.

Furthermore, exposing the object under investigation to fast neutrons requires additional radiation protection for the chamber in order to comply with the current national requirements for protection of the personnel and population against the effect of ionizing radiation, which leads to an increase in the mass and dimensions of a unit implementing the prior art method. Also, an increase of the radiation dose absorbed by the object under investigation takes place, which can cause a deterioration of consumer properties of industrial articles contained therein, e.g. electronic equipment and photographic materials.

For the above reasons, the most effective in explosive detection are those methods equipment units (U.S. Pat. No. 5,078,952, 1992; U.S. Pat. No. 5,153,439, 1992; U.S. Pat. No. 5,200,626, 1993; EP 0336634, 1993; WO 91/14938) that are based on the combined use of X-ray radiography and neutron radiation analysis using thermal neutrons or thermal and fast neutrons simultaneously. All prior art methods of explosive detection of the above-discussed type include the initial positioning of an object under investigation into an X-ray unit; exposing the object under investigation to X-rays; recording the X-rays that have passed through the object under investigation to form one or more X-ray images of the object under investigation; next positioning the object under investigation into the radiation-protected chamber; exposing the object under investigation to thermal neutrons or to thermal and fast neutrons simultaneously; recording the secondary 10.8 MeV gamma radiation and emitted by the object under investigation during radiation capture of thermal neutrons by nuclei of nitrogen-14 atoms, or recording the secondary 10.8 MeV gamma rays and secondary 6.1 MeV gamma rays emitted by nuclei of oxygen-16 atoms in exited state formed as a result of the interaction between fast neutrons and stable nuclei of oxygen-16 atoms; and making a decision about the presence of an explosive in the object under investigation on the basis of an analysis of both the X-ray image of the object under investigation and the distribution of nitrogen or nitrogen and oxygen therein.

The combined use of X-ray radiography and neutron radiation analysis provides greater probability of correct explosive detection; however, it does not relieve the mentioned prior art methods from the above disadvantages inherent to each of these groups of methods individually.

Besides, the use of all above described prior art methods of explosive detection that are based on the neutron radiation analysis of materials provides for the irradiation by neutrons of the entire volume of the object under investigation. This requires, first, the use of a source with a large flow of fast neutrons, so that the predetermined detection characteristics could be attained. This leads to an increase in the mass and dimensions of the unit implementing the method, due to the necessity of additional radiation protection measures, and increases the cost of the unit. Second, this makes it necessary to expose to neutrons the areas of the object under investigation that do not contain an explosive, but may contain non-explosive nitrogen- and oxygen-containing materials, which materials, after the exposure to thermal and fast neutrons, will emit gamma rays. As a result, the probability of false alarms will increase. Third, the unnecessary neutron irradiation of areas of the object under investigation that do not contain an explosive increases the radiation dose absorbed by articles within the object under investigation, e.g. electronic equipment and photographic materials, which can cause an impairment of their consumer qualities.

The closest prior art to the proposed invention is constituted by a method of detecting arms and explosives in objects under investigation (RU 2065156, 1996), said method being based on the combined use of X-ray radiography and neutron radiation analysis. The prior art method of detecting arms and explosives in objects under investigation includes the following steps:

exposing an object under investigation to X-rays;

recording X-rays that have passed through the object under investigation;

using an X-ray image of the object under investigation to detect areas with a density of inorganic and organic materials exceeding pre-established threshold values;

determining in these areas a geometric shape of articles with a density of inorganic materials exceeding the established threshold value;

further exposing the areas of the object under investigation with a density of organic materials exceeding the established threshold value to thermal neutrons produced by a thermal neutron radiator in the form of a radionuclide californium-252-based source;

recording the secondary 10.8 MeV gamma radiation emitted by the exposed areas of the object under investigation and using, as informative parameters for arms and explosive detection, the value of X-ray attenuation by the object under investigation depending on the atomic numbers of chemical elements present in the composition of materials within the object under investigation and on the X-ray wavelength, geometrical shape of areas with a density of inorganic materials exceeding the established threshold value, and the intensity of the secondary gamma radiation recorded.

As noted above, during the transition from an exited state to the ground state only an average of 14 nuclei of nitrogen atoms in 100 nuclei of atoms that have captured thermal neutrons emit a 10.8 MeV gamma-ray quantum, whereas the rest of said nuclei emit two or more gamma-ray quanta with lower energies, i.e. only about 14% of the mass of nitrogen contained in an explosive emits gamma rays used as one of the basic informative parameters. This circumstance leads, on the one hand, to an increase in the explosive detection threshold when using this or other prior art methods. On the other hand, this makes it necessary to establish lower threshold value for the intensity of secondary 10.8 MeV gamma rays in order to provide the required probability of correct explosive detection, which, in its turn, leads to a greater probability of a false alarm due to the presence in the object under investigation of other, non-explosive nitrogen-containing materials.

Therefore, the described method, like all other prior art methods using X-ray radiography and the neutron radiation analysis in which the areas of an object under investigation with a density of organic materials higher than the established threshold value are exposed to thermal neutrons, does not allow ensuring the required low probability of a false alarm, since the presence of an explosive is only judged by the value of intensity of 10.8 MeV gamma rays during radiation capture of thermal neutrons by nuclei of nitrogen-14 atoms. In this case, the presence in the object under investigation of materials that are not explosive, but contain nitrogen in quantities similar to its content in explosives may lead to wrong decisions.

Since the number of recorded gamma-ray quanta greatly depends on the position of the neutron-exposed area of the object under investigation emitting secondary gamma rays relative to the gamma-ray detector, primarily on the distance between them, the results of recording gamma-ray quanta are much affected by the location of that area within the volume of the object under investigation. Ignoring their relative position in the prior art methods leads to a distortion of results of gamma radiation recording, which may cause omission of the explosive, thus reducing the probability of correct detection.

The use in the state-of-the-art methods of an once-established invariable threshold value for overall intensity of gamma rays, which value stays constant in a fairly wide range of change in possible masses of explosives being detected, requires using a very low threshold value sufficient enough to detect an explosive, including that having a minimal mass, with the predetermined probability of correct detection. Using such a low threshold value corresponding to the minimal mass of an explosive will considerably increase probability of false alarms caused by gamma rays emitted by non-explosive nitrogen-containing materials and by nitrogen of air.

Moreover, in practicing any of all existing methods based on the neutron radiation analysis the use of a thermal neutron radiator that has an invariable directional pattern, with its emitting surface forming a rather wide divergent beam of thermal neutrons, does not make it possible to expose to thermal neutrons a small-size area having a density of organic materials greater than the established threshold value. This leads to the inevitable neutron irradiation of adjacent areas of the object under investigation that may contain non-explosive nitrogen-containing materials as well as air. As a result, gamma rays are emitted by the non-explosive nitrogen-containing materials and the nitrogen of air contained in areas of the object under investigation adjacent to the area being exposed, which also increases the probability of a false alarm.

Furthermore, the prior art methods do not ensure a high level of radiation safety for the reason that, as a rule, they make use of a radionuclide neutron source, which may lead to radioactive contamination of the environment in emergency situations caused by an explosion or fire, as well as to irradiation of the population, should the source be embezzled. Irradiating many areas of an object under investigation with a density of organic materials higher that the established threshold value also leads to an unjustified increase of the radiation dose absorbed by articles contained in objects under investigation, which may result in an impairment thereof.

Where a check is required on the presence of small masses of explosive in small-size objects under investigation, e.g. mail wrappers and hand luggage of passengers such as bags, briefcases, video and photographic cameras, portable computers, mobile phones and the like, these objects are positioned for neutron exposure in a radiation-protected chamber with dimensions meant for checking the luggage or mailings of significantly larger dimensions. Consequently, the cavity can contain a considerable amount of air not replaced by the object under investigation. When exposed to thermal neutrons, air will also emit gamma rays which, given the appreciable volume of remaining air, either will preclude a small mass of explosive from being detected or may cause a false alarm due to the high background component of gamma rays from nitrogen of air present in the radiation-protected chamber.

In addition, virtually all known state-of-the-art methods do not include a step of the identification, by its X-ray image, of an article contained in the area of the object under investigation and having a density of organic materials higher than the established threshold value. The absence of such information about the presence of such compact article in the area of the object under investigation being exposed to thermal neutrons decreases a probability of correct explosive detection and does not make it possible to reduce the probability of a false alarm.

For the same reason, the existing methods provide during the neutron radiation analysis for the exposure to thermal neutrons of all areas of the object under investigation with a density of organic materials exceeding the established value, which greatly extends the entire explosive detection time.

As shown by the above-presented analysis of the existing explosive detection methods, still unresolved to date remain major problems stemming from an insufficiently high probability of correct detection, a high probability of false alarms, an increased detection threshold of an explosive being detected, a prolonged time of explosive detection, an insufficient level of radiation safety, and a high probability of deterioration of consumer properties of certain industrial goods contained in an object under investigation as a result of checking. This accounts for the absence in the arsenal of security services of modern facilities ensuring a highly efficient and rapid explosive detection in an object under investigation.

DISCLOSURE OF THE INVENTION

The primary object of the present invention is to increase the probability of correct explosive detection.

A further object of the present invention is to reduce the probability of a false alarm when detecting an explosive in an object under investigation.

A still further object of the present invention is to decrease, by implementing the method of the invention, a detection threshold for an explosive in an object under investigation.

The object of the present invention is also to reduce the overall time of detecting an explosive in an object under investigation.

In addition, the object of the present invention is to heighten the level of radiation safety and decrease a danger of impairment of consumer properties of the object or of articles contained therein as a consequence of its exposure to neutrons.

Other objects and advantages of the present invention will be made clear below in examining the preferred embodiment of the invention and graphic materials illustrating it.

According to the present invention, the set objects are achieved by the following steps included in the proposed method of detecting an explosive in an object under investigation:

exposing the object under investigation to X-rays;

recording the X-rays that have passed through the object under investigation and finding, on a basis of a rate of X-ray attenuation, areas of the object under investigation with a density of organic materials exceeding a pre-established value;

identifying, on a basis of an analysis of the recorded X-rays, articles present in the aforementioned found areas of the object under investigation with said density of organic materials exceeding the pre-established value, and selecting, among said areas, an area containing an unidentified article;

determining, on a basis of an analysis of the recorded X-rays, dimensions and a position of said unidentified article within the object under investigation;

evaluating a mass of explosive being detected, on a basis of the dimensions of the unidentified article and, for instance, the average density of existing explosives;

determining and forming a directional pattern of a thermal neutron radiator corresponding to the dimensions of the unidentified article and exposing the selected area of the object under investigation to thermal neutrons from said neutron radiator preferably arranged as a controlled thermal neutron radiator with variable directional pattern based on the deuterium-deuterium reaction and equipped with a neutron moderator;

recording, using at least two gamma-ray detectors, gamma-ray quanta with the energy of 10.8 MeV and pairs of simultaneously emitted cascade gamma-ray quanta, preferably, with the energy of 5.534 MeV and 5.266 MeV from said selected area;

determining an overall intensity of gamma rays emitted by the object under investigation, preferably, by summing up numbers of 10.8 MeV gamma-ray quanta recorded by each of the gamma-ray detectors, said numbers multiplied by a weight factor of each corresponding detector readings, and numbers of pairs of cascade gamma-ray quanta, simultaneously recorded by each of pairs of gamma-ray detectors, multiplied by the weight factor of said pair of detectors, wherein the weight factor of a detector is determined, e.g., experimentally, taking into account the position of the unidentified article relative to the given gamma-ray detector, and the weight factor of said pair of detectors is determined, e.g., as the arithmetical mean of weight factors of detectors comprising that pair;

determining a threshold value for the overall intensity of gamma rays emitted by the object under investigation, basing on the supposed mass of explosive being detected and making a decision about presence of the explosive within the object under investigation if the threshold value is exceeded by overall intensity of the gamma rays emitted by the object under investigation.

Optionally, when detecting an explosive in a small-size object under investigation, the mass of air surrounding the object under investigation is reduced before its exposure to thermal neutrons, preferably by replacing it by a gaseous medium free from nitrogen.

The recording not only 10.8 MeV gamma-ray quanta emitted by the irradiated area of the object under investigation, but also 5.534 MeV and 5.266 MeV cascade gamma-ray quanta with the use of at least two gamma-ray detectors, the count of pairs of cascade gamma-ray quanta recorded simultaneously, the determination of the overall gamma-ray intensity and comparison of the latter with the threshold value yield a higher probability of correct explosive detection or a lower minimal mass of explosive detectable by the method of the invention, which is confirmed by the following reasoning.

As noted above, during the transition from exited state to ground state an average of only 14% of nuclei of nitrogen atoms that have captured thermal neutrons emit gamma-ray quanta having the energy of 10.8 MeV. However, another 19% of nuclei of nitrogen atoms, on the average, make this transition in two steps through an intermediate exited state lasting not longer than $10^{-15}$ s. During such two-step transition to the ground state a nucleus of nitrogen atom, due to negligible time of staying in intermediate exited state, emits in different directions and virtually simultaneously two cascade gamma-ray quanta with the energy of 5.534 MeV and 5.266 MeV, respectively. Since cascade gamma-ray quanta composing a pair are emitted in different directions, their recording requires, as a rule, use of two gamma-ray detectors.

An additional recording 5.534 MeV and 5.266 MeV cascade gamma-ray quanta makes it possible to capture gamma rays emitted, on the average, not by 14%, but by 33% of nuclei of nitrogen atoms that have captured thermal neutrons, As a results, an increase in the overall intensity of recorded of and, thus, in the informative value of the method are attained. In other words, the combined recording 10.8 MeV gamma-ray quanta and cascade gamma-ray quanta increases the probability of correct detection at preset values of the probability of false alarms and minimal mass of an explosive to be detected.

However, in difference to 10.8 MeV gamma-rays, a direct recording 5.534 MeV and 5.266 MeV cascade gamma-ray quanta is practically unfeasible owing to the presence of gamma rays with quantum energies within a range of 5–6 MeV emitted during the interaction of thermal neutrons with nuclei of atoms of a number of other chemical elements, e.g., sulfur, chlorine and sodium. Hence, in case of direct recording, presence of additional cascade gamma-ray quanta from said elements can lead to false alarms.

This is why the methods of the present invention provides for checking the coincidence in time of the moments of receiving two gamma-ray quanta with the energies of 5.534 MeV and 5.266 MeV by two gamma-ray detectors in order to ascertain that the aforementioned two gamma-ray quanta constitute a pair of cascade gamma-ray quanta emitted by a single nucleus of a nitrogen atom as a result of the two-step transition from the exited state to the ground state, but not by nuclei of atoms of other chemical elements.

Locating the area of the object under investigation containing an unidentified article and having a density of organic materials exceeding the established value; determining the dimensions and position of the unidentified article within the object under investigation; determining and forming a directional pattern of the thermal neutron radiator corresponding to the dimensions of the unidentified article; exposing to thermal neutrons only said located area; recording gamma-ray quanta by several, at least by two, gamma-ray detectors positioned at different distances from the area being irradiated; and determining the overall intensity of gamma rays emitted by the object under investigation with taking into account the weight factor of readings of each of the detectors and those of pair(s) of detectors, results in providing more information for use in detecting an explosive and, thus, increases the probability of correct detection.

Determining the position of the unidentified article within the object under investigation on the basis of an analysis of X-rays recorded makes it possible to establish the weight factor of readings of each gamma-ray detector on the basis of relative position of the unidentified article and gamma-ray detector and so to determine the overall gamma-ray intensity by summing up, with appropriate weight factors, numbers of 10.8 MeV gamma-ray quanta and numbers of pairs of cascade gamma-ray quanta simultaneously recorded by each of pairs of gamma-ray detectors.

Since the proposed method provides for recording gamma-ray quanta by several, at least by two, gamma-ray detectors, the result of recording gamma-ray quanta by each of them will have its own weight determined by the position of each gamma-ray detector relative to the area exposed to thermal neutrons.

Therefore, the proposed method provides for experimentally determining, during the calibration, weight factors of readings of detectors which allow for the distance between a gamma-ray detector and the area of the object under investigation exposed to thermal neutrons, as well as for inherent efficiency and sensitivity anisotropy of each gamma-ray detector, the scattering of gamma-ray quanta, the dimensions and mass of an explosive used for calibration. This also ensures a greater probability of correct explosive detection.

Use of the steps of determining the dimensions of an unidentified article inside the object under investigation on the basis of an analysis of X-rays recorded; assessing the supposed mass of an explosive being detected on the basis of the dimensions of the unidentified article and the average density of existing explosives; determining the threshold value for overall gamma-ray intensity on the basis of the supposed mass of the explosive being detected; and making a decision on the presence of the explosive in the object under investigation, should that threshold value be exceeded by overall gamma-ray intensity ensures a rational choice of a threshold value for overall gamma-ray intensity in accordance with the supposed mass of an explosive being detected. This, in its turn, leads to a greater probability of correct explosive detection and a lower probability of false alarms.

The proposed method makes it possible, on the basis of the dimensions of an unidentified article obtained from the analysis of X-rays recorded and the average density of existing explosives, to approximately estimate the mass of the unidentified article in the instance where the latter is an explosive. Obtaining an estimate of the supposed mass of an explosive being detected on the basis of results of X-ray radiography monitoring and using the estimate as a priori information for the operation of neutron radiation analysis of the object under investigation in accordance with the present invention makes it possible to most efficiently determine a threshold value for overall gamma-ray intensity that allows for the supposed mass of an explosive being detected, which mass corresponds to the dimensions of the unidentified article, and yields the highest value of correct detection probability ever possible under these conditions.

Besides, using an invariable threshold value for overall gamma-ray intensity established without regard to the a priori information about the supposed mass of an explosive being detected would require choosing a fairly low threshold value sufficient enough to detect the minimal mass of explosive with the preset probability of correct detection. Using such a low threshold value corresponding to the minimal mass of explosive will lead to false alarms caused by gamma rays emitted by non-explosive nitrogen-containing materials and nitrogen of air.

In the instance where the results of X-ray radiography monitoring show that the supposed mass of an explosive being detected is considerably higher than the minimal mass, the proposed method makes it possible to increase the threshold value for overall gamma-ray intensity in accordance with the value of supposed explosive mass without noticeably reducing correct detection probability, but rather leading to a significantly lower probability of a said false alarms.

Finding the area of the object under investigation that contains an unidentified article and has a density of organic materials higher than the established value; determining the dimensions and position of the unidentified article within the object under investigation; determining and forming a directional pattern of thermal neutron radiator corresponding to the dimensions of the unidentified article; and exposing to thermal neutrons only the area of the object under investigation containing the unidentified article make it possible, on the one hand, to expose the whole volume of the unidentified article to thermal neutrons and, on the other, not to expose to thermal neutrons areas of the object under investigation that are adjacent to the unidentified article and may contain non-explosive nitrogen-containing materials. The first circumstance makes the whole volume of the unidentified article emit gamma rays, thus increasing the overall intensity of gamma rays recorded and leading to a higher probability of correct explosive detection. The second circumstance accounts for a lesser gamma radiation emitted by non-explosive nitrogen-containing materials present in the areas of the object under investigation adjacent to the unidentified article, which means a lower probability of a false alarm.

In addition, exposing to thermal neutrons revealing only the area containing an unidentified article reduces the overall time of explosive detection thanks to exclusion from neutron radiation analysis the areas with a density of organic materials greater than the established value with all articles contained therein being identified.

Irradiating by thermal neutrons only a limited area of the object under investigation and using for this purpose a controlled thermal neutron radiator with a variable directional pattern, which radiator is based on the deuterium-deuterium reaction and is equipped with a neutron moderator, precludes exposing to thermal neutrons other areas of the object under investigation known to contain no explosive.

First, this increases the level of radiation safety; second, decreases the probability of impairing consumer properties of such goods as photographic materials and electronic equipment due to exposure to neutrons; third, prevents non-explosive nitrogen-containing materials from thermal neutron exposure, which areas will not in this case emit secondary gamma rays that may lead to a false alarm.

Reducing, before thermal neutron exposure, the mass of air surrounding the object under investigation through replacing air by, e.g., a gaseous nitrogen-free medium lowers the probability of a false alarm that may be caused by gamma rays emitted by nitrogen contained in the air, or diminishes the minimum explosive mass detected over invariable gamma radiation recording time with the preset probabilities of correct detection and false alarm, thanks to a lower background component of nitrogen in the air inside the radiation-protected chamber.

This is particularly important in the instance where a check is required on the presence of an explosive in small-size objects under investigation, e.g., mail wrappers and passenger hand luggage such as bags, briefcases, video and photographic cameras, portable computers, mobile phones and the like. When small objects are placed for thermal neutron exposure in the radiation-protected chamber having dimensions designed for checking considerably larger objects, its cavity will inevitably contain a substantial volume of air not replaced by the object under investigation. When exposed to thermal neutrons, the remaining air will also emit gamma rays. The volume of said air being great enough, this can cause a false alarm or prevent a small explosive mass from being detected owing to the significant background component of gamma rays of nitrogen in the air.

The aforementioned circumstances confirm that the declared objects and technical result of the present invention are achieved thanks to the fact that the proposed invention has characteristic features listed above.

The aforementioned objects and other objects, as well as advantages of the invention, will become more obvious from the below description of the preferable invention embodiment and accompanying drawings.

BRIEF DESCRIPTION OF THE DRAWINGS

The following graphic materials illustrate the realization of the preferred embodiment of the method of the present invention.

DESCRIPTION OF THE PREFERRED EMBODIMENT OF THE INVENTION

Figure 1:
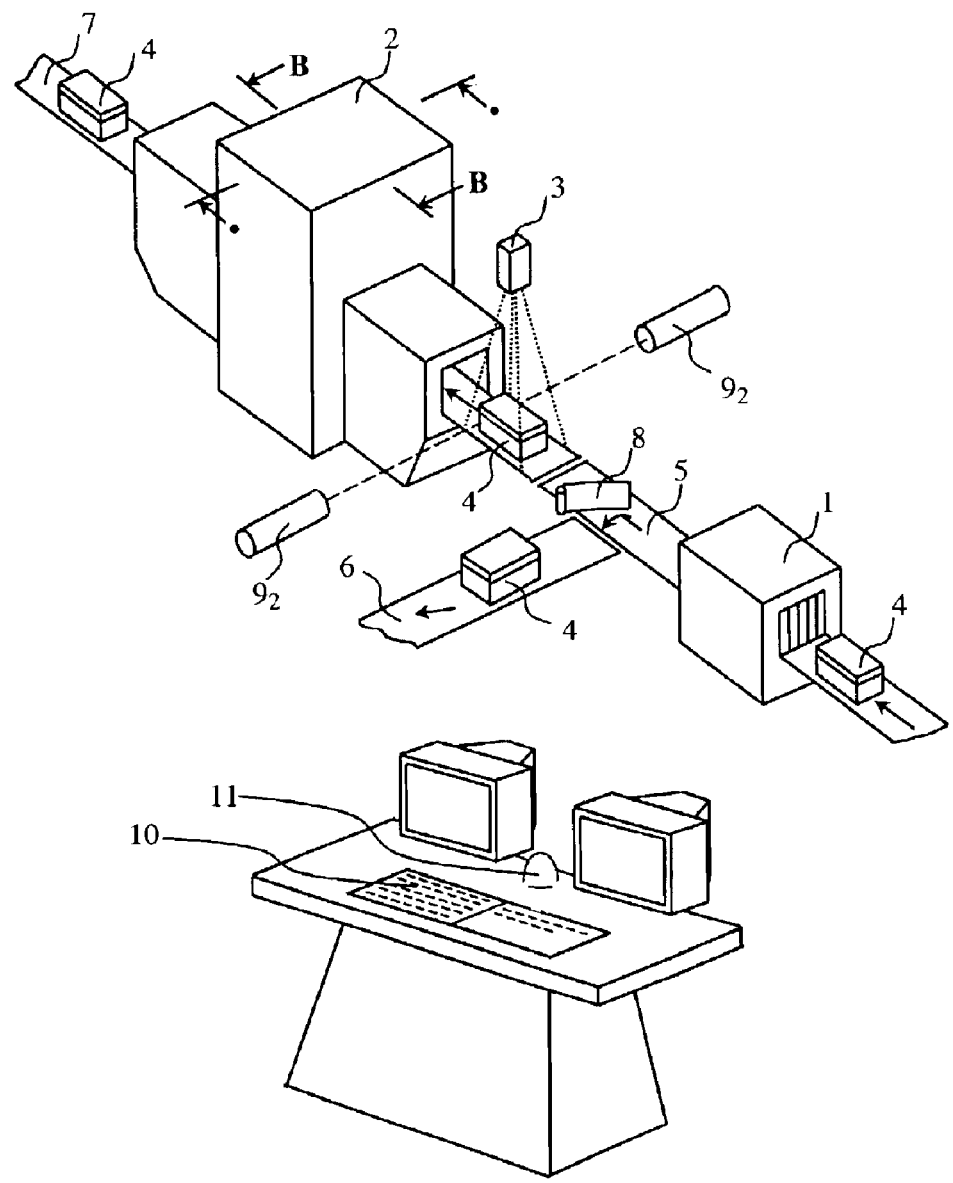
FIG. 1 shows a general view of a system implementing the inventive method.
Figure 2:
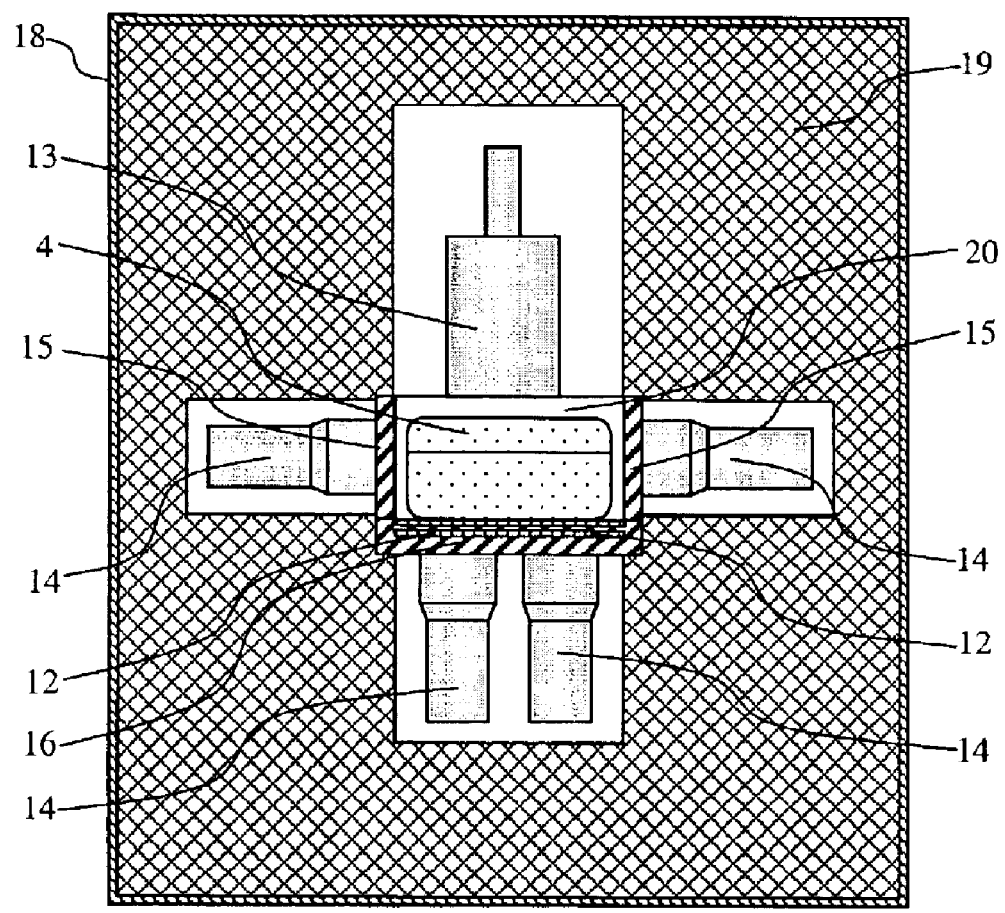
FIG. 2 shows a cross section along A—A of a unit for neutron radiation analysis incorporated in the system for detecting an explosive in an object under investigation.
Figure 3:
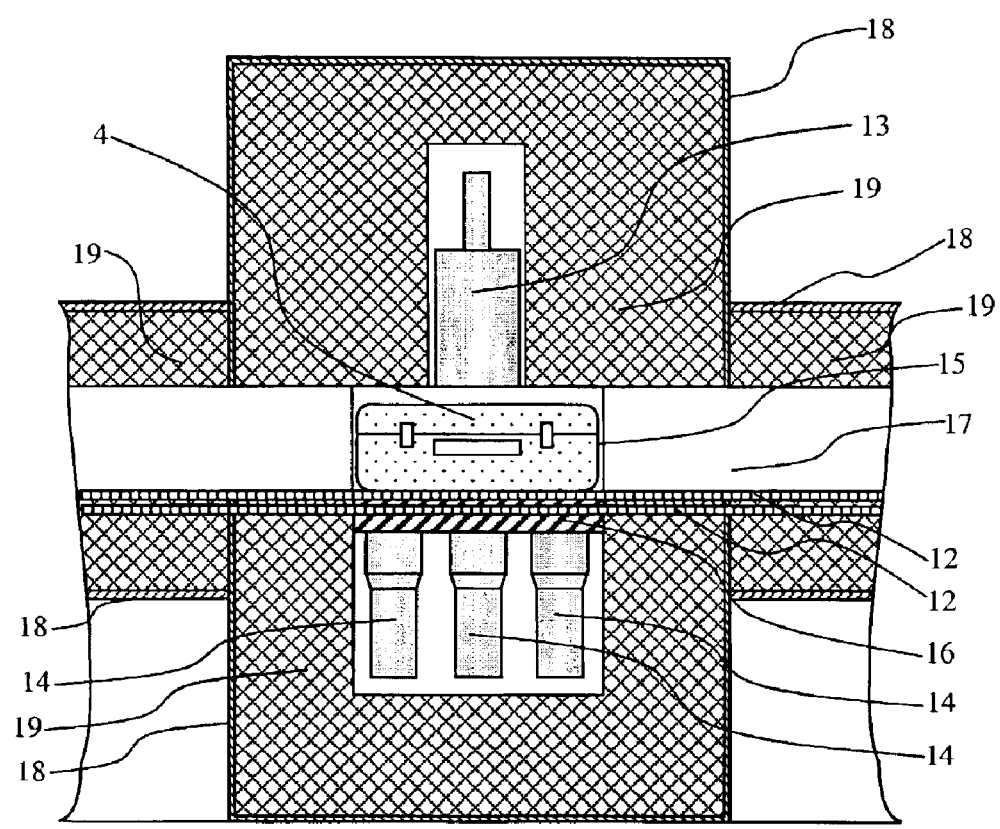
FIG. 3 shows a longitudinal section along B—B of the unit for neutron radiation analyses incorporated in the system for detecting an explosive.
Figure 4:
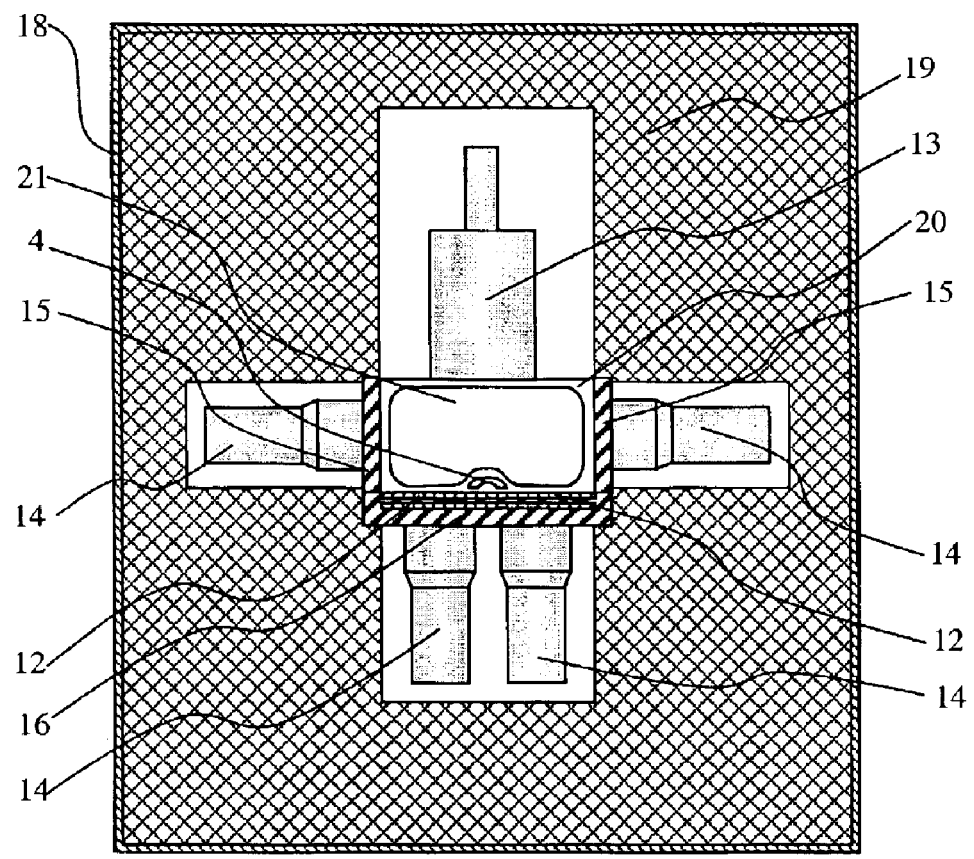
FIG. 4 shows a cross section along A—A of the unit for neutron radiation analyses in the event of detecting an explosive in a small-size object, e.g., in a mobile phone.
Figure 5:
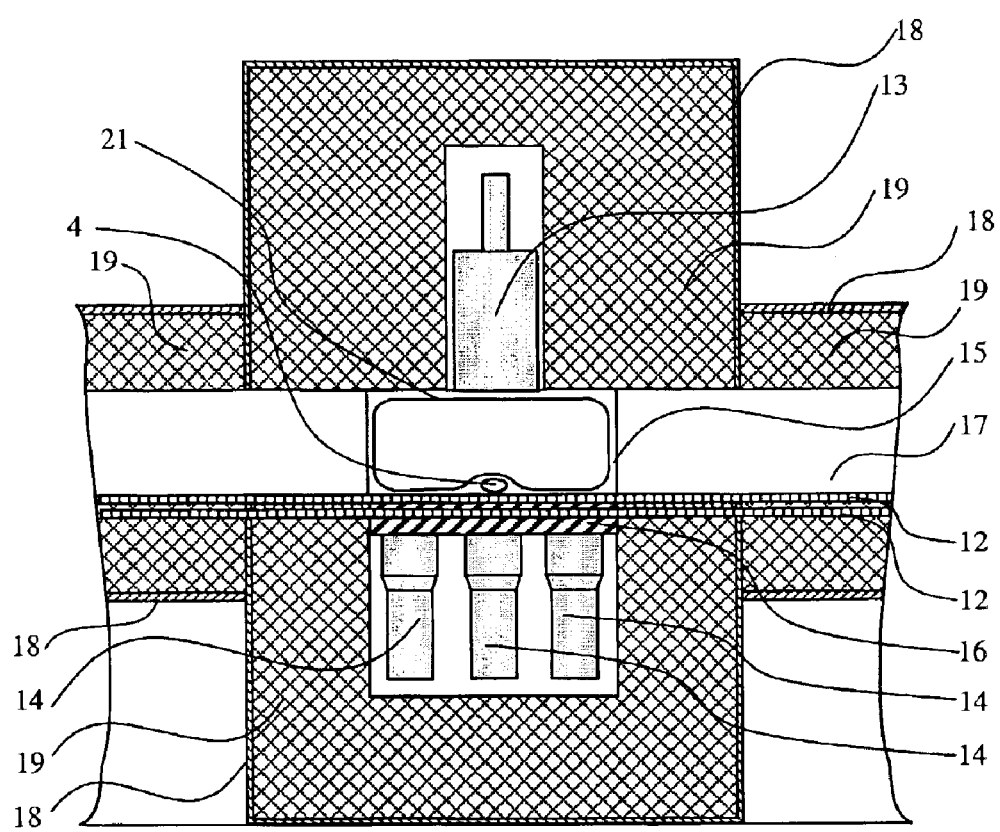
FIG. 5 shows a longitudinal section along B—B of the unit for neutron radiation analyses in the event of detecting an explosive in a small-size object, e.g., a in mobile phone.

The preferred embodiment of the method for detecting an explosive in an object under investigation according to the present invention comprises the following steps:

first, an object under investigation is placed in an X-ray unit and exposed to X-rays;

the X-rays that have passed through the object under investigation are recorded, and at least two digital X-ray images of the object under investigation are formed in different, preferably orthogonal, projections;

on the basis of an analysis of the X-ray images, the areas of the object under investigation are found which have a density of organic materials exceeding a pre-established value;

after that, articles contained in the said areas with the density of organic materials exceeding the pre-established value are identified on the basis of an analysis of its X-ray images. If all articles contained within these areas have been identified and classified as articles not containing an explosive, then checking the object under investigation is terminated. If some article is identified as containing an explosive, the object under investigation is directed for inspection;

the area of the object under investigation is found which has a density of organic materials exceeding the established value and contains an unidentified article;

the dimensions and position of the unidentified article in the object under investigation are determined on the basis of X-ray images;

the volume of the unidentified article is determined on the basis of its dimensions; then the mass of an explosive being evaluated, which corresponds to the dimensions of the unidentified article, is computed, taking into account the average density of existing explosives, e.g. selected from the range of 1.25 to 2.00 g/cm$^3$;

basing on the obtained dimensions of the unidentified article, the required minimum directional pattern of the controlled thermal neutron radiator is determined which pattern is necessary to expose to thermal neutrons the whole volume of the unidentified article in accordance with its dimensions; the obtained minimum directional pattern of the controlled thermal neutron radiator is then set up;

the object under investigation is placed in a radiation-protected chamber, and only the area of the object under investigation containing the unidentified article is exposed to thermal neutrons emitted by the controlled thermal neutron radiator having a variable directional pattern, the radiator preferably being based on the deuterium-deuterium reaction and equipped with a neutron moderator;

during a period T, gamma-ray quanta of the secondary gamma radiation emitted by the area being exposed to thermal neutrons are recorded by M gamma-ray detectors ($M \geq 2$), which convert light flashes resulting from the interaction of gamma-ray quanta with the scintillator of the detector into electric pulses having amplitudes proportional to the energy of gamma-ray quanta. Only electric pulses with amplitudes proportional to the gamma-ray quantum energies of 10.8 MeV, 5.534 MeV and 5.266 MeV are selectively detected;

one counts the number $N_i$ of electric pulses with an amplitude proportional to the 10.8 MeV gamma-ray quanta recorded over the period T by each detector from the set M of gamma-ray detectors;

electric pulses from pairs of cascade gamma-ray quanta are selected on the basis of coincidence in time of electric pulses with amplitudes proportional to the 5.534 MeV and 5.266 MeV gamma-ray quanta;

one counts the number $K_{ij}$ (proportional to the second component of overall gamma-ray intensity) of pairs of cascade gamma-ray quanta recorded over the period T by each pair of gamma-ray detectors numbered as "i" and "j" from the set M of gamma-ray detectors;

the logarithm of likelihood ratio is calculated as follows:

$$L = \sum_{i=1}^{M} (w_i N_i - N_{0i}) + \sum_{i=1}^{M-1} \sum_{j=i+1}^{M} (w_{ij} K_{ij} - K_{0ij}),$$

where:

$w_i$, $w_{ij}$ are the weight factors of readings of the ith and jth gamma-ray detectors. These weight factors are determined experimentally during the calibration stage and allow for the distance between the detectors and the area of the object under investigation being exposed to thermal neutrons, as well as for inherent efficiency and sensitivity anisotropy of the gamma-ray detectors, the scattering of gamma-ray quanta, the dimensions and mass of the explosive used during the calibration;

$N_{0i}$ is the average count of 10.8 MeV gamma-ray quanta made by the ith gamma-ray detector over the period T. This count is obtained experimentally during preliminary calibration of the system implementing the method of the invention with the use of an explosive whose mass is equal to the calculated supposed mass of explosive corresponding to the dimensions of the unidentified article;

$K_{0ij}$ is the average count of pairs of cascade gamma-ray quanta produced by said pair of gamma-ray detectors over the period T. This count is obtained experimentally during preliminary calibration of the system realizing the method with the use of an explosive whose mass is equal to the calculated supposed mass of explosive corresponding to the dimensions of the unidentified article;

the obtained logarithm L of likelihood ratio is compared with the low and upper threshold values equal, respectively, to $L_1 = \ln((1-P_D)/(1-P_{FA}))$ and $L_2 = \ln(P_D/P_{FA})$, where $P_D$ is the required probability of correct explosive detection in the object under investigation and $P_{FA}$ is the required probability of a false alarm. Such comparison is made by known sequential probability ratio test (see Wald A., Wolfowitz J. Optimum character of the sequential probability ratio test. Ann. Math. Statistics, 1948, V.326, p.19).

If the comparison shows that the logarithm of likelihood ratio is less than the low threshold value ($L<L_1$), then a decision is made about the absence of an explosive, and checking the object under investigation is terminated. If the logarithm of likelihood ratio exceeds the upper threshold value ($L>L_2$), then a decision is made about the presence of an explosive, and the object under investigation is directed for inspection. If the value of the likelihood ratio logarithm lies between the low and upper threshold values ($L_1<L<L_2$), then a decision about the presence or absence of an explosive cannot be made with the required probabilities of correct detection and a false alarm.

In the latter case, the check is continued by making one more neutron radiation analysis of the object under investigation with repeated exposure to thermal neutrons, recording the secondary gamma radiation and repeating the decision-making procedure provided for by the proposed method.

In addition, if it is necessary to detect an explosive in a small-size object under investigation whose dimensions are considerably smaller that those of the cavity of the radiation-protected chamber, once the object under investigation is positioned in it and, before the exposure to thermal neutron, the air is displaced from the chamber by, e.g., a gaseous nitrogen-free medium, such as carbon dioxide, in order to decrease the mass of remaining air.

FIG. 1 shows a general view of a system implementing the preferred version of the method according to the present invention. The system comprises an X-ray unit 1; a first conveyor 5 passing through an inner cavity of the X-ray unit 1; a second conveyor 6; a unit 2 for neutron radiation analyses; a third conveyor 7 passing through an inner cavity of the unit 2; a video camera 3 positioned above the third conveyor 7 in front of the entrance to the inner cavity of unit 2; and a butterfly gate 8 installed in such a way that it can be driven to rotate above the belt of the first conveyor 5 at the exit from the X-ray unit 1 where the belt of the second conveyor 6 adjoins the first conveyor. The first conveyor 5 moves the object 4 under investigation through the horizontal shaft of the X-ray unit 1. The second conveyor 6 transports the object 4 away from the checking zone if an analysis of its X-ray image has not shown the presence therein of areas with a density of organic materials higher than the established value or if the analysis has shown the presence of said areas, but all articles contained therein have been identified and classified as not containing an explosive. The third conveyor 7 is designed to transport the object 4 through the horizontal shaft of unit 2 for neutron radiation analyses and is made capable of stopping with a short run-out. A sensor 9 of position of the object 4 under observation comprises an optical source $9_1$ and an optical detector $9_2$. The system comprises also an equipment 10 of an operator's working place and an alarm indicator 11.

For the X-ray unit 1 there can be used, e.g., the existing X-ray systems for luggage inspection Z-SCAN designed and produced by Perkin Eimer Instruments (former EG&G Astrophysics Research Corporation), Long-Beach, Calif., USA, and also X-ray tomographic systems of CTX-5000 SP and CTX-5500 DS types designed and produced by In Vision Technologies, Foster City, Calif., USA, which systems make it possible to obtain at least two X-ray images of an object 4 in different projections. For instance, the luggage inspection system Z-SCAN contains a radiation-protected casing with a horizontal shaft, through which the first conveyor 5 passes; an X-ray tube with an X-ray collimator; a scintillator made, e.g., from cadmium tungstate; a photodiode array; a unit of analog-to-digital converters; information processing equipment; a control desk; and a data representation unit in the form of a color display. The control desk and data representation unit are incorporated in equipment 10 of the operator's working place.

Electronic equipment processing signals and information from the unit 2 for neutron radiation analyses is also included into equipment of the operator's working place 10, which contains an alarm indicator 11.

Figure 11:
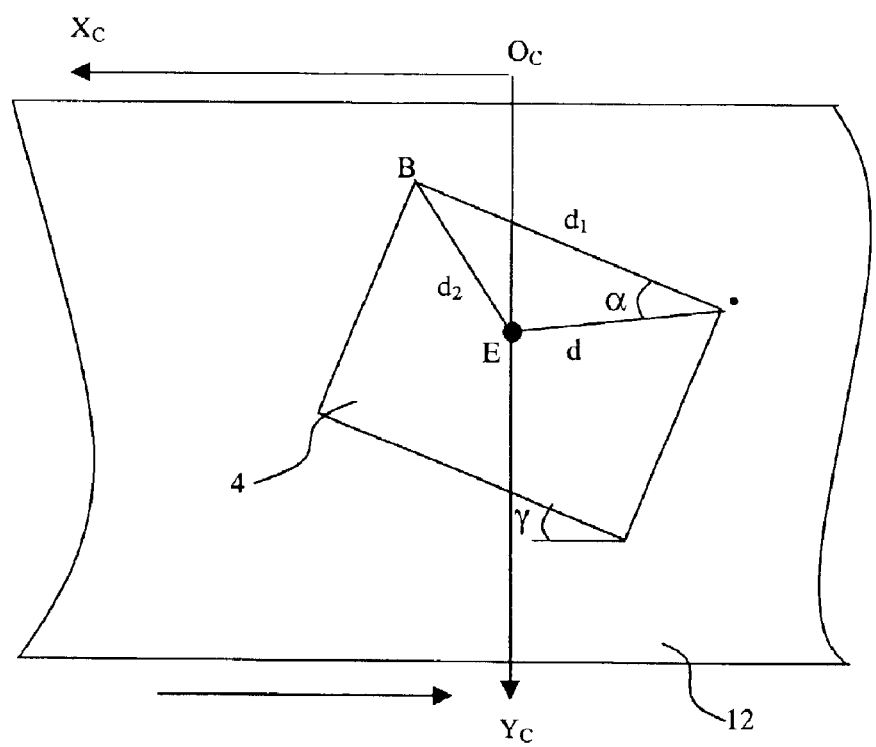
FIG. 11 shows the position of an object under investigation on the conveyor belt in a chamber of the unit for neutron radiation analyses and the coordinate system $X_C O_C Y_C$ connected with said chamber.

The unit 2 for neutron radiation in analyses presented in FIGS. 2 to 5 comprises a casing 18 with a radiation shielding 19 inside it made from polyethylene doped with boron to reduce the level of neutron radiation and from lead to reduce the level of gamma rays to acceptable values. A horizontal shaft 17 with a belt 12 of the third conveyor 7 located in its lower part passes through the casing 18 and radiation shielding 19. In the central part of the horizontal shaft 17 is a chamber 20 formed by two side neutron reflectors 15 and a bottom neutron reflector 16 and designed to house the object 4 while exposing it to thermal neutrons. The side neutron reflectors 15 and the lower neutron reflector 16 are made from polyethylene in the shape of plates with dimensions not smaller than the respective overall dimensions of the chamber 20. The reflectors are positioned, respectively, vertically and horizontally, flush with respective walls of the chamber. The side and the bottom neutron reflectors 15 and 16 are designed to increase the amount of thermal neutrons by slowing down, in the material of reflectors, fast neutrons emitted by a controlled thermal neutron radiator 13, and also to provide uniform distribution of thermal neutrons throughout the area of the object 4 being irradiated. The controlled thermal neutron radiator 13 is positioned above the chamber 20 in a cavity made in radiation shielding 19 on the axis $O_C Y_C$ of coordinate system $X_C O_C Y_C$ (FIG. 11) connected with the chamber 20. The radiator 13 is arranged to be moved by an appropriate driving means above the belt 12 of the third conveyor 7 along axis $O_C Y_C$ in the plane perpendicular to the direction of movement of the belt 12. Gamma-ray detectors 14 are positioned in cavities made in radiation shielding 19, below the chamber 20 and on its two sides, respectively, behind the bottom neutron reflector 16 and the side neutron reflectors 15. The object position sensor 9 containing the optical source $9_1$ and the optical detector $9_2$ (FIG. 1) is positioned at the entrance to the horizontal shaft 17 of the unit 2 and provides means to stop the belt 12 with the object 4 in front of the entrance to the horizontal shaft 17 in order to obtain an image of said object with the video camera 3.

In addition, a fluid-tight elastic envelope 21 (FIGS. 4 and 5) is installed above the chamber 20 in a cavity made in radiation shielding 19. The fluid-tight elastic envelope 21 has a pipeline and electro-pneumatic valve to feed compressed carbon dioxide used in detecting an explosive in the small-size object 4 and shown in these figures in a state of being filled with carbon dioxide. The fluid-tight elastic envelope 21 filled with carbon dioxide serves to displace nitrogen-containing residual air from the chamber 20 when the small-size object 4 with dimensions considerably smaller than those of chamber 20 is subjected to neutron exposure.

Figure 6:
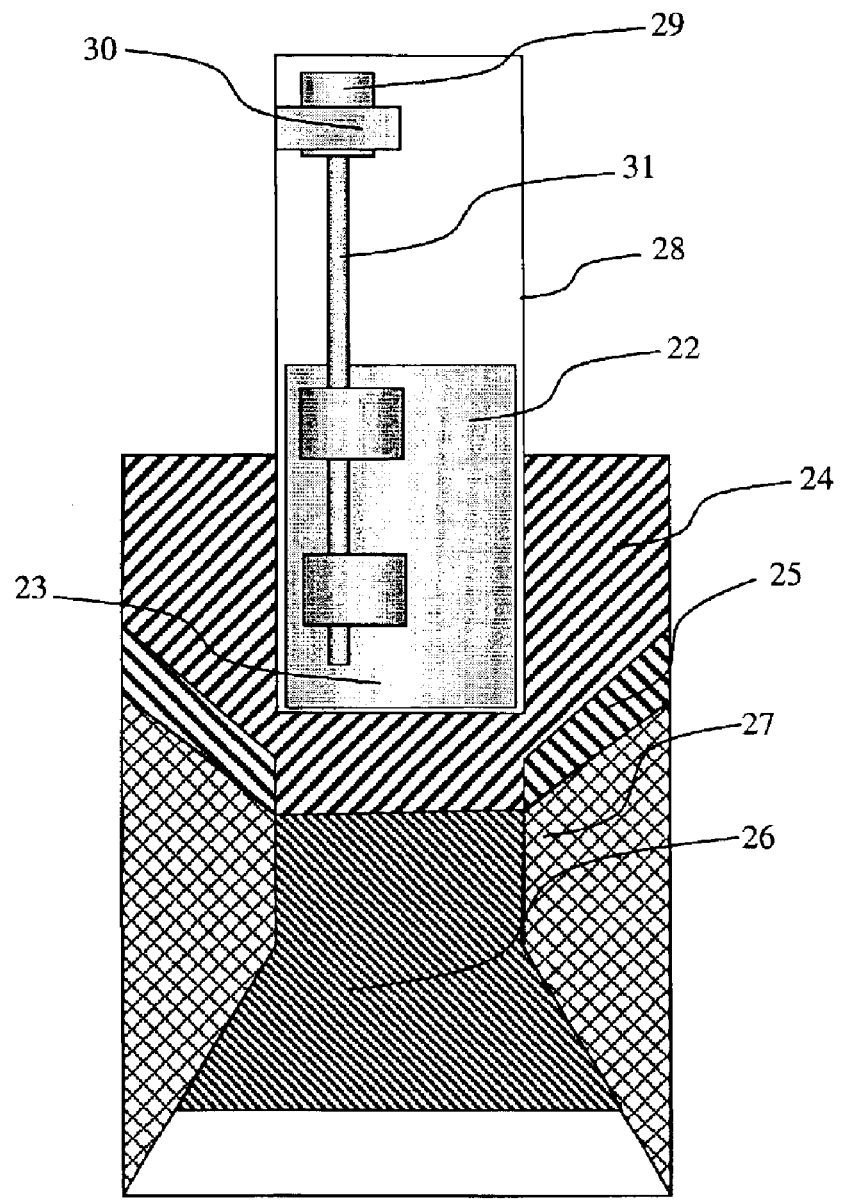
FIG. 6 shows a longitudinal section of a controlled radiator of thermal neutrons.

As shown in FIG. 6, the controlled thermal neutron radiator 13 comprises a neutron source 22 with a target 23 installed in a cup 28 of source made, e.g., from aluminum. The neutron source 22 can be moved axially inside the cup 28 by a worm gearing 31 driven by a step electric motor 29 which is fixed on the cup 28 with the help of a yoke 30. The cup 28 with the neutron source 22 inside is surrounded by a neutron moderator 24 made, preferably, from graphite. In addition, the controlled radiator 13 contains a neutron reflector 25 made, e.g., from polyethylene and surrounding the neutron moderator 24. The radiator 13 further comprises a filter 26 adjoining the neutron moderator 24 and installed in the orifice of the neutron reflector 25, and a collimator 27 surrounding a filter 26. The filter 26 is preferably made from bismuth, while collimator 27 is made from polyethylene with addition of boron.

For the neutron source 22 it is preferable to use a neutron source based on the deuterium-deuterium reaction. The sources of this type are produced, for example, by Kaman Nuclear, Colorado, USA, or by Sodern, France. They are capable to generate fast neutrons with the energy of about 2.3 MeV. The neutron moderator 24 reduces kinetic energy of fast neutrons to the energy of about 0.025 eV. The neutron reflector 25 is designed to prevent neutrons from leaking through the lateral surface by returning them to the volume of the neutron moderator 24. The filter 26 attenuates the flow of fast neutrons and capture gamma radiation emitting to the chamber 20, while the collimator 27 is designed to form a beam of thermal neutrons with its cross-section area equal to that of the zone of the object 4 being exposed to neutrons. The electric motor 29 with the worm gearing 31 provides reversible axial displacement of the neutron source 22 within the cup 28 of the source, which makes it possible to enlarge or narrow the directional pattern of the controlled thermal neutron radiator 13.

Figure 7:
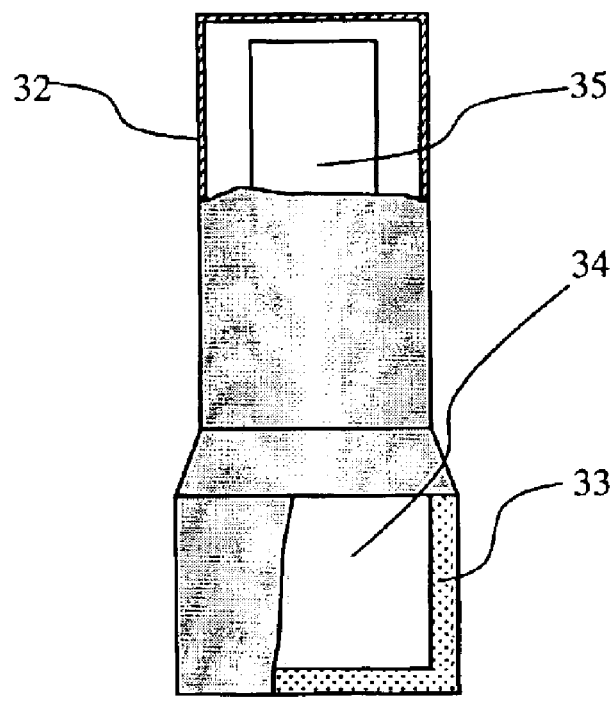
FIG. 7 shows a longitudinal section of a gamma-ray detector.

FIG. 7 shows a longitudinal section of the gamma-ray detector 14. The detector 14 comprises a detector housing 32 with a photomultiplier 35 inside it. The optical photomultiplier 35 is in contact with a scintillator 34 placed in a cup 33 of neutron filter. For the scintillator 34 it is most preferable to use an inorganic scintillating material based, e.g., on thallium-activated sodium iodide. To reduce the effect of thermal neutrons penetrating from the chamber 20 on the scintillator 34, it is positioned in the cup 33 of neutron filter, which is made hermetic with double walls and a double bottom, the cavity between them being filled with a material reducing the flow of thermal neutrons, preferably, with lithium carbonate, lithium fluoride or lithium phosphate.

Figure 8:
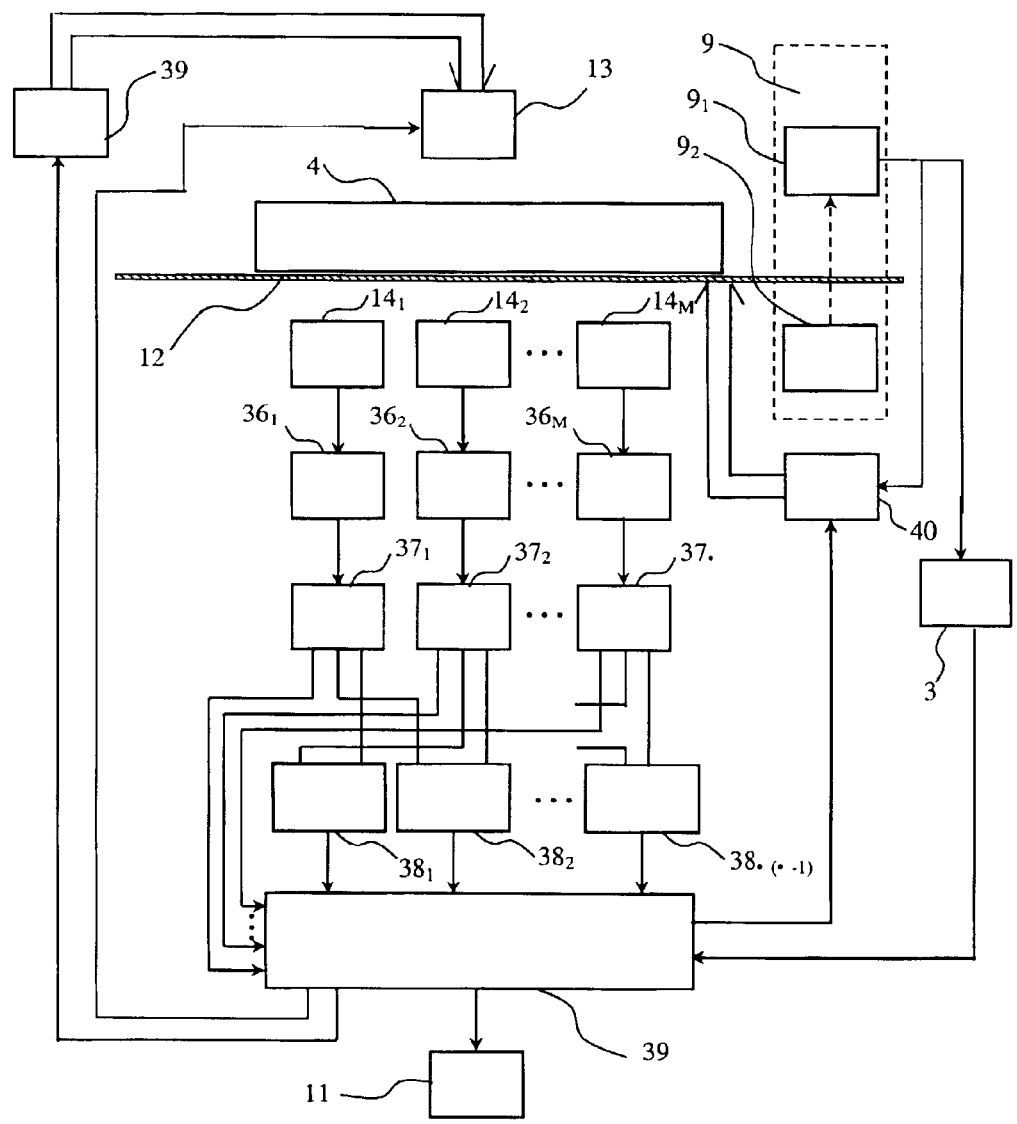
FIG. 8 shows a block diagram of electronic equipment used to make a neutron radiation analysis and incorporated in the system for detecting an explosive in an object under investigation.

FIG. 8 shows a block diagram of electronic equipment constituting a part of the unit 2 for neutron radiation analyses and of the equipment 10 of the operator's working place. The electronic equipment comprises M gamma-ray detectors $14_1$–$14_M$ connected, via M amplifiers $36_1$–$36_M$, to inputs of M amplitude analyzers $37_1$–$37_M$. Each amplitude analyzer $37_1$–$37_M$ is built on the basis of comparators and has three outputs. First output of each amplitude analyzer $37_1$–$37_M$ is connected directly to the computer 41 and serves to transmit electric pulses formed during recording gamma-ray quanta with the energy of 10.8 MeV. Second and a third outputs of each amplitude analyzer $37_1$–$37_M$, for example, amplitude analyzer $37_1$ are connected, in parallel with, respectively, third and second outputs of each remaining (M−1) amplitude analyzers $37_2$–$37_M$, to two inputs of M(M−1) coincidence circuits $38_1$–$38_{M(M-1)}$ Said outputs serve to transmit electric pulses formed during recording cascade gamma-ray quanta with the energies of, respectively, 5.534 MeV and 5.266 MeV. The outputs of M(M−1) coincidence circuits $38_1$–$38_{M(M-1)}$ are connected to a computer 41 to transmit thereto electric pulses formed during the recording pairs of cascade gamma-ray quanta by all possible pairs of gamma-ray detectors $14_1$–$14_M$.

Video camera 3, which is capable of forming a digital image signal and is positioned above the belt 12 of the third conveyor 7 in front of the entrance to the horizontal shaft 17, is connected to the computer 41 input to transmit a digital signal of the image of the object 4 located on the belt 12 of third conveyor 7 in front of the entrance into the horizontal shaft 17. In addition, an output of X-ray unit 1 is connected to the computer 41 input to transmit a digital signal of X-ray images of the object 4.

A first computer 41 output is connected to an input of a drive 39 of neutron radiator which enables the controlled thermal neutron radiator 13 to make reversible displacements above the belt 12 of third conveyor 7 along axis $O_C Y_C$ (FIG. 11) in the plane perpendicular to the direction of movement of the belt 12. A second computer 41 output is connected to an input of the alarm indicator 11 designed to produce signals warning of the presence or absence of an explosive in the object 4. A third computer 41 output is connected to the first input of the control unit 40 for controlling the third conveyor 7 by sending a signal to stop the third conveyor 7 when the object 4 is moved into a preset position within the chamber 20, and a signal to start the third conveyor 7 after a neutron radiation analysis of the object 4 in the chamber 20 is completed. A fourth computer 41 output is connected to the step electric motor 29 of the controlled thermal neutron radiator 13 to make it possible to transmit pulses in number corresponding to the required lengthwise axial displacement of neutron source 22 to a position ensuring a directional pattern of the controlled thermal neutron radiator 13 necessary to irradiate an unidentified article of certain dimensions.

Figure 10:
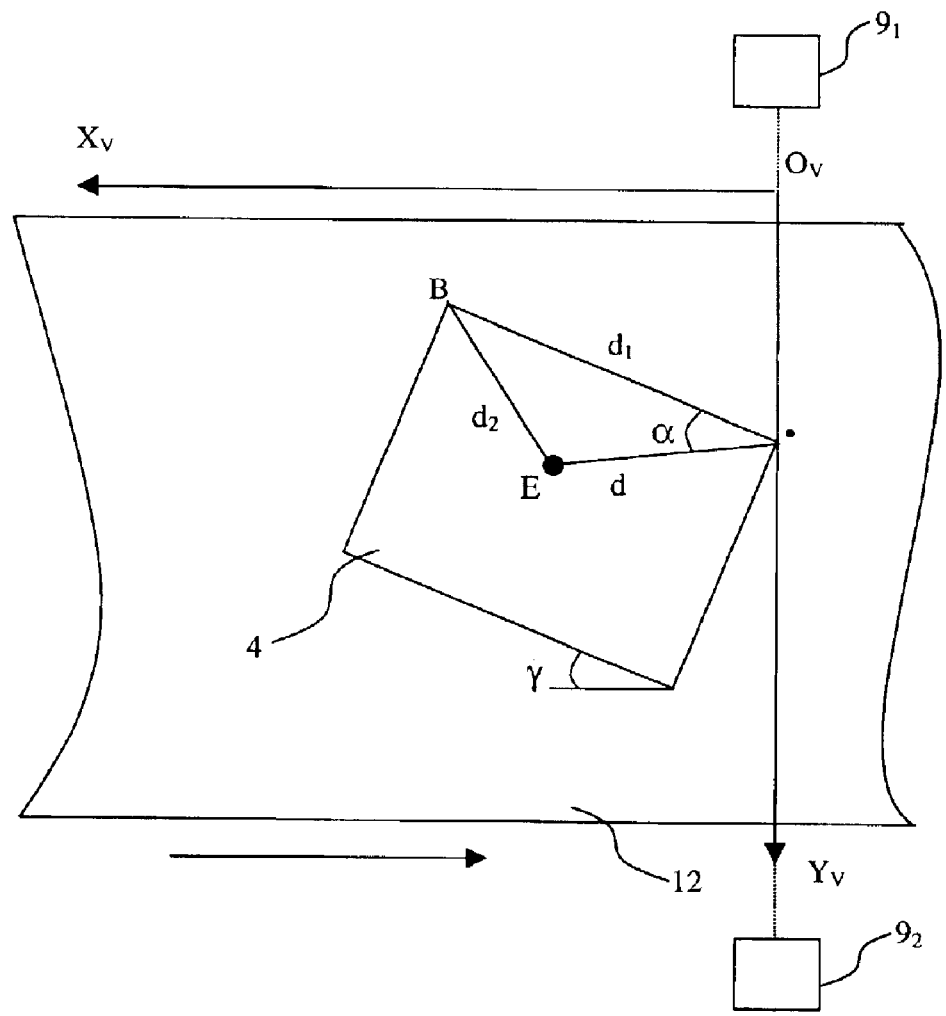
FIG. 10 shows a position of an object under investigation on the conveyor belt within the field of view of a video camera incorporated in the system for detecting an explosive in front of the entrance of the unit for neutron radiation analyses and a coordinate system $X_V O_V Y_V$ connected with the video camera.

The sensor 9 of position of the object 4 can be an optoelectronic sensor in the form of an optic source $9_1$, e.g., emitting radiation within an infrared wavelength range, and an optical detector $9_2$ having matched spectral sensitivity. The sensor 9 (FIGS. 1 and 8) is positioned above the belt 12 of third conveyor 7 between the video camera 3 and the entrance to the horizontal shaft 17 along axis $O_V Y_V$ of coordinate system $X_V O_V Y_V$ (FIG. 10) so that, when the forward end of the moving object 4 enters its field of vision, the entire object 4 is within the video camera's 3 field of view. An output of the sensor 9 is connected to the input of video camera 3 for switching it on and to the second input of the control unit 40 for the third conveyor 7 for transmitting a signal to stop it after the object 4 has been moved into the video camera's 3 field of view.

A system implementing the preferred embodiment of the proposed method of detecting an explosive in an object under investigation functions as follows.

An operator performing the check places the object 4 on the first continuously moving conveyor 5 (FIG. 1) which carries the object 4 to the X-ray unit 1 such as, e.g., the X-ray luggage inspection system Z-SCAN making it possible to obtain two X-ray images of the object 4 in different projections. While the first conveyor 5 transports the object 4 through the X-ray unit, the object 4 is exposed to X-rays.

When X-rays are passing through the object 4, they lose in intensity owing to the absorption and scattering by materials contained in the object 4, the absorption degree being the higher the greater are atomic numbers of chemical elements present in the composition of these materials. Since organic materials consist primarily of chemical elements with low values of atomic numbers, whereas inorganic materials predominantly contain chemical elements with higher atomic numbers, the energy of X-rays recorded will be determined by whether this radiation passes through organic or inorganic materials contained in the object 4. As a result of recording X-rays in two energy ranges, the X-ray unit 1 makes it possible to form images of organic materials in orange and those of inorganic materials in blue on the screen of the sensor display of equipment 10 at the operator's working place. An image is colored green when organic and inorganic materials are superimposed within the volume of the object 4 or when a material has a very high density. Forming a colored X-ray image of the object 4 makes its analysis convenient for the operator, since weapons are depicted green on the display screen, inorganic materials that cannot enter into the composition of an explosive are depicted blue, whereas organic materials, potentially an explosive, are depicted orange.

Basing on the analysis of a colored X-ray picture, the operator establishes, first of all, the presence of arms and areas with a high density of organic materials in the object 4. If they are absent in the object 4, then the butterfly gate 8 positioned across the belt of the first conveyor 5 transfers the object 4 to the belt of second conveyor 6 which removes that object 4 from the checking zone. Having detected arms (by a green colored mage and by their characteristic geometric shape) in the object 4, the operator removes the object 4 from the first conveyor 5 and sends it for inspection.

If the object 4 contains no arms, but has an area with a density of organic materials exceeding the established value, which can be identified by the saturation of orange color in an X-ray picture, then the operator proceeds to identifying articles present in that area on the basis of geometric shape of their X-ray images. If, as a result of identification, these articles have been classified as not containing an explosive, then the second conveyor 6 removes the object 4 from the checking zone, as described above.

Figure 9:
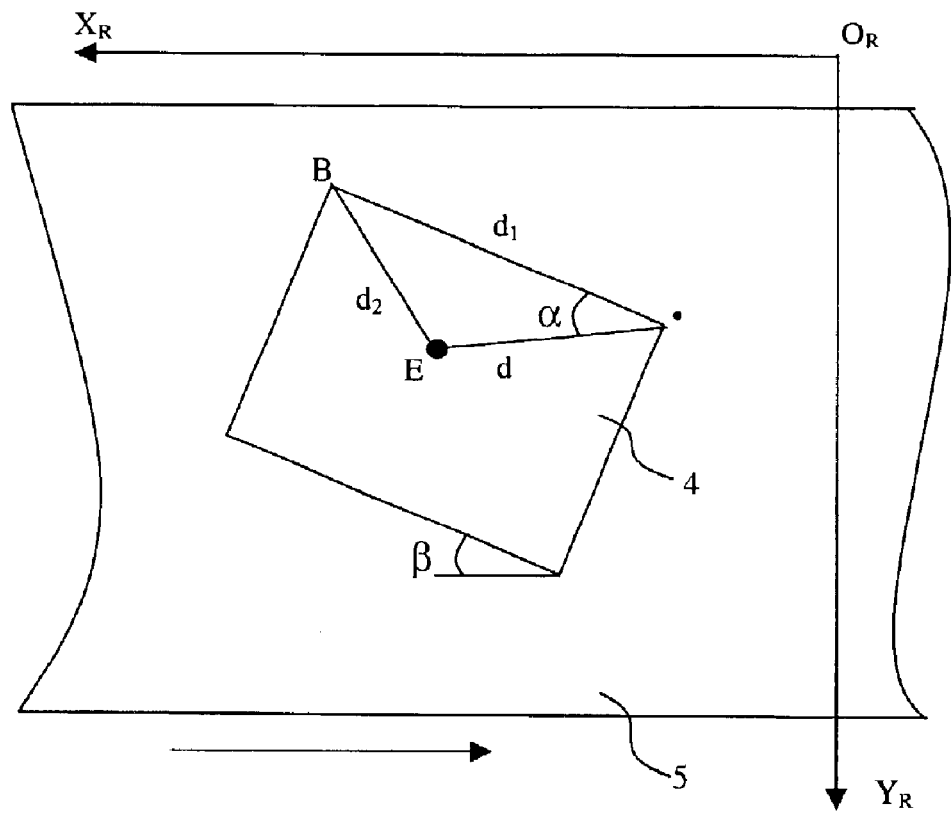
FIG. 9 shows the position of an object under investigation on the conveyor belt in an X-ray unit incorporated in the system for detecting an explosive in an object under investigation and a coordinate system $X_R O_R Y_R$ connected with the X-ray unit.

If the operator is not able to identify confidently an article present in the suspected area of the object 4 as not containing an explosive, then he or she marks the center of the unidentified article by touching with a pointer the respective spot on the sensor display reproducing the X-ray image at the operator's working place. The computer 41 automatically receives data on coordinates $x_R^E$, $y_R^E$ of the center (point E) of the unidentified article within the $X_R O_R Y_R$ coordinate system (FIG. 9) connected with the X-ray unit 1; and at least two digital X-ray images of the object 4 obtained by the X-ray unit 1 in two different, preferably orthogonal, projections.

After processing the digital X-ray image of the object 4 corresponding to its top view, the computer 41 calculates coordinates $x_R^A$, $y_R^A$ and $x_R^B$, $y_R^B$ of respectively, corner points A and B of the object 4 in its arbitrary position on the belt of first conveyor 5, e.g., at an angle β to the longitudinal axis of the conveyor belt. Basing on coordinates of the center (point E) of the unidentified article and corner points A and B of the object 4, the computer 41 then calculates the distance d and angle α (FIG. 9), which determine the position of the center of the unidentified article within the object 4 by the following expressions:

$$d=((x_R^A-x_R)^2+(y_R^A-y_R^E)^2)^{1/2},\ \alpha=\arccos((d^2+d_1^2-d_2^2)/(2dd_1)),$$

$$d_1=((x_R^A-x_R^B)^2+(y_R^A-y_R^B)^2)^{1/2},\ d_2=((x_{R'-x_R}^B)^2+(y_R^E-y_R^B)^2)^{1/2}.$$

Then, basing on the results of processing the digital X-ray image of the object 4 corresponding to its top view, the computer 41 determines the maximum overall dimension of the unidentified article and chooses, out of data stored in its memory, a value closest to the obtained maximum overall dimension of the unidentified article. During calibration of the unit 2 for neutron radiation analyses, at the step of putting the system into operation, data must be entered to the computer 41 memory about possible values of the maximum overall dimension of the unidentified article and values corresponding to them and determining the required lengthwise axial position of the neutron source 22 inside the cup 28 of the source of the controlled thermal neutron radiator 13 (FIG. 6). Such a required lengthwise axial position of the neutron source 22 enables to obtain a minimally possible directional pattern of the controlled thermal neutron radiator 13, which later on will make it possible, on the one hand, to irradiate the entire volume of an unidentified article and, on the other, to irradiate only the area of the object 4 that is limited by the maximum overall dimension of the unidentified article. Subsequently, this will exclude a possibility of exposing to thermal neutrons areas of the object 4 adjacent to the unidentified article.

As indicated above, the computer 41 chooses a value from data stored in its memory which corresponds to the nearest maximum overall dimension obtained for the unidentified article and has the form of a digital code of the number of pulses to be fed to the step electric motor 29 of the controlled thermal neutron radiator 13 in order to longitudinally displace the neutron source 22 to a position in which the required minimally possible directional pattern of the controlled thermal neutron radiator 13 will be attained. The aforementioned number of pulses from the computer 41 output are sent to the step electric motor 29 of the radiator 13, and the latter longitudinally displaces the neutron source 22 to the required position with the aid of worm gearing 31.

In addition, basing on the results of processing two digital X-ray images of the object 4, the computer 41 calculates an approximate volume of the unidentified article and then, taking into account the average density of existing explosives lying within a range of 1.25 to 2.00 g/cm$^3$, evaluate the mass of an explosive which the unidentified article can contain.

Then a signal from computer 41 activates the third conveyor 7 and the butterfly gate 8 is driven to turn so as to bar a way for the object 4 to the second conveyor 6, but open a way to the third conveyor 7.

The first conveyor 5 and then the third conveyor 7 move the object 4 to the entrance of horizontal shaft 17 of the unit 2 for neutron radiation analyses. When the forward end (point A) of the moving object 4 reaches the sensor 9 (FIGS. 1, 8 and 10), it will intercept the optical beam from the optical source $9_1$ of the sensor 9 to its optical detector $9_2$, with the result that sensor 9 forms an electric signal that is transmitted to the video camera 3 (and switches it on) and to the control unit 40, which stops the third conveyor 7.

Video camera 3 forms a digital signal corresponding to an image of the object 4, e.g., in a binary form, and this signal is entered into the computer 41. After processing the binary image of the object 4, the computer 41 uses the coordinate system $X_VO_VY_V$ (FIG. 10), connected with the video camera 3 and the sensor 9, to calculate coordinates $y_V^A$ and $x_V^B$, $y_V^B$ of corner points A and B (coordinate $x_V^A=0$) of the object 4 which is in an arbitrary position on the belt of the conveyor 7 at the angle γ to the conveyor's longitudinal axis. Angle γ allows for possible displacement of the object 4 relative to its initial position on the belt of first conveyor 5 at the angle β to the conveyor's longitudinal axis. Then, using coordinates of corner points A and B, the computer 41 calculates the angle γ by the expression $\gamma=\arctg((y_V^A-y_V^B)/x_V^B)$.

Using the expressions $x_V^E=d\cos(\alpha-\gamma)$, $y_V^E=d\sin(\alpha-\gamma)+y_V^A$ the computer 41 further calculates coordinates of the position of the center (point E) of the unidentified article in the object 4 within the coordinate system $X_VO_VY_V$ connected with the video camera 3 and the sensor 9.

The above operations determine coordinates of the center (point E) of the unidentified article within the coordinate system connected with the video camera 3 and the sensor 9 and, thus, help to allow for possible displacement of the object 4 relative to its initial position on the belt of the first conveyor 5 which can occur while the object 4 is transported from the first conveyor 5 to the third conveyor 7.

The computer 41 then forms a signal for the control unit 40 and the control unit 40 activates the third conveyor 7 for a preset interval of time necessary to move the object 4 to a certain distance into chamber 20 of the unit 2 for neutron radiation analyses, after which the third conveyor 7 will be stopped. This distance is equal to the sum of coordinate $x_V^E$ of the center (point E) of the unidentified article within the coordinate system $X_VO_VY_V$ (FIG. 10) connected with the video camera 3 and the sensor 9, and a preset fixed distance between origins of coordinates of the coordinate system $X_VO_VY_V$ connected with the video camera 3 and the sensor 9 and the coordinate system $X_CO_CY_C$ connected with chamber 20 and the controlled thermal neutron radiator 13 movably positioned on axis $O_CY_C$. As a result of such movement of the object 4, the center (point E) of the unidentified article will be on axis $O_CY_C$ of the coordinate system $X_CO_CY_C$.

Simultaneously, computer 41 sends, in the form of a digital code, the coordinate $y_C^E=y_V^E$ of the center (point E) of the unidentified article within the coordinate system $X_CO_CY_C$ to the drive 39 of the neutron radiator which converts said digital code. Basing on the number of pulses in the sequence, a step motor incorporated in the drive 39 of the neutron radiator displaces the radiator 13 to a distance equal to coordinate $y_C^E$ of the center of the unidentified article, thus making a projection of the center of the emitting surface of the radiator 13 on a horizontal plane to coincide with the center of the unidentified article.

If the object 4 has small overall dimensions compared to those of chamber 20, then the operator presses relevant keys on the computer 41 keyboard to enter a command for the displacement of residual air out of chamber 20. By that command, computer 41 sends a signal to an electro-pneumatic valve of the fluid-tight elastic envelope 21, and the valve opens a pipeline connecting the fluid-tight elastic envelope 21 with a vessel containing compressed carbon dioxide. Fluid-tight elastic envelope 21, while being filled with carbon dioxide, displaces the main volume of residual air from the chamber 20. After carbon dioxide pressure in the fluid-tight elastic envelope 21 reaches a preset value, the electro-pneumatic valve is closed.

Thereafter, computer 41 forms a signal transmitted to the controlled thermal neutron radiator 13 to activate the neutron source 22. This results in the radiator 13 emitting fast neutrons with the energy of about 2.3 MeV (FIG. 6), which are slowed down in the neutron moderator 24 to the thermal energy of about 0.025 eV and then are formed by collimator 27 into a beam with its cross section area equal to that of the neutron-exposed zone of the object 4 containing an unidentified article.

Said collimated beam of thermal neutrons irradiates the area of the object 4 containing the unidentified article. Exposing the nitrogen-containing materials in said area to thermal neutrons brings about the radiation capture of thermal neutrons by nuclei of nitrogen-14 atoms, resulting in the formation of nuclei of nitrogen-15 atoms in exited state. The transition of nuclei of nitrogen-15 atoms from exited to ground state will be accompanied by the emission of gamma-ray quanta with the energy of 10.8 MeV and transition probability of around 0.14 or by a virtually simultaneous emission in different directions of two cascade gamma-ray quanta with the energies of 5.534 and 5.266 MeV and transition probability of about 0.19.

Some part of said gamma-ray quanta will enter the scintillators 34 of gamma-ray detectors $14_1$–$14_M$ (FIG. 7) and cause light flashes therein with a brightness proportional to the energies of gamma-ray quanta. Photo-electronic multiplier 35 of gamma-ray detectors $14_1$–$14_M$ convert optical radiation emitted by the scintillators 34 into electric pulses with amplitudes proportional to the energies of gamma-ray quanta that have entered scintillators 34. After their amplification by amplifiers $36_1$–$36_M$ (FIG. 8), the pulses are fed to the amplitude analyzers $37_1$–$37_M$.

Amplitude analyzers $37_1$–$37_M$ select the pulses with amplitudes proportional to the energies of gamma-ray quanta with the result that the pulses with amplitudes proportional to the gamma-ray quantum energies of 10.8 MeV, 5.534 MeV and 5.266 MeV are sent, respectively, to the first, second and third outputs of amplitude analyzers $37_1$–$37_M$.

The pulses with amplitudes proportional to the gamma-ray quantum energy of 10.8 MeV are sent from the first output of amplitude analyzers $37_1$–$37_M$ to the computer 41, which counts their number during the period T. In this way the number $N_i$ (proportional to one component of overall gamma-ray intensity) of 10.8 MeV gamma-ray quanta recorded over the time T by each detector from the set M of gamma-ray detectors $14_1$–$14_M$ will be determined.

The pulses with amplitudes proportional to the gamma-ray quantum energies of 5.534 MeV and 5.266 MeV are sent from, respectively, the second and third outputs of amplitude analyzers $37_1$–$37_M$ to the inputs of coincidence circuits $38_1$–$38_{M(M-1)}$. A coincidence pulse is formed at the output of each coincidence circuit $38_1$–$38_{M(M-1)}$ only when two pulses with amplitudes proportional to the gamma-ray quantum energies of 5.534 MeV and 5.266 MeV simultaneously arrive at its inputs.

Coincidence pulses are sent from the outputs of coincidence circuits $38_1$–$38_{M(M-1)}$ to the inputs of computer 41 which counts their number during a period T. In this way the number $K_{ij}$ (proportional to the second component of overall gamma-ray intensity) of pairs of cascade gamma-ray quanta recorded over the time T by each pair constituted by the ith detector and by the jth detector from the set of M gamma-ray detectors $14_1 14_M$ is determined.

The computer 41 then calculates the logarithm L of likelihood ratio as was explained above, in the course of describing the preferred embodiment of the method of the present invention. Then, as was also explained above, the computer 41 compares the obtained logarithm L of likelihood ratio with the low and upper threshold values $L_1$ and $L_2$.

If the comparison shows that the logarithm of likelihood ratio is less than the low threshold value ($L<L_1$), the computer 41 sends a signal to the control unit 40 to activate the third conveyor 7. It also sends an appropriate signal to the alarm indicator 11, which warns the operator about the absence of an explosive. The checking of the object 4 is completed, and the third conveyor 7 carries it from the checking zone.

If the logarithm of likelihood ratio exceeds the upper threshold value ($L>L_2$), the computer 41 sends a signal to the control unit 40 to activate the third conveyor 7. The third conveyor 7 moves the object 4 from the horizontal shaft 17 of unit 2 and, after the object 4 leaves the horizontal shaft 17, the third conveyor 7 is stopped by a signal from the computer 41 transmitted via the control unit 40. Simultaneously the computer 41 forms a signal about the presence of an explosive in the object 4 and sends it to the alarm indicator 11, which makes it known to the operator. The operator removes the object 4 from the third conveyor 7 and sends it for inspection.

If the value of the logarithm of likelihood ratio lies between the low and upper threshold values ($L_1<L<L_2$), a decision about the presence or absence of an explosive cannot be made with the required probabilities of correct detection and false alarm. In this case, in order to continue checking by making one more neutron radiation analysis of the object 4, the computer 41 again activates the controlled thermal neutron radiator 13, which again exposes to thermal neutrons the area of the object 4 containing the unidentified article.

The system realizing the proposed method further operates in a manner similar to that described above. A distinction is that the computer 41 counts both 10.8 MeV gamma-ray quanta and cascade gamma-ray quanta recorded over the time T and sums up corresponding counts with those of corresponding gamma-ray quanta recorded over the same time T in the previous checking cycle. As a result, the logarithm of likelihood ratio is formed and its comparison with threshold values is made, taking into account the number of gamma-ray quanta recorded over the overall time equal to 2T.

If, upon expiration of the set number of similar checking cycles, a decision about the presence or absence of an explosive in the object 4 cannot be made with the required probabilities of correct detection and false alarm, then the computer 41 sends a signal to the control unit 40 to activate the third conveyor 7. The third conveyor 7 carries the object 4 from the horizontal shaft 17. After the object 4 leaves the horizontal shaft 17, the third conveyor 7 is stopped by a signal from the computer 41 transmitted via the control unit 40. Simultaneously, the computer 41 forms a signal about the failure to make a final decision on the presence or absence of an explosive in the object 4 and sends it to the alarm indicator 11. The operator then takes the object 4 off the third conveyor 7 and sends it for inspection.

The inventors have developed and made prototype samples of a system for detecting an explosive in the luggage of air travelers, which samples employing the principles of the present invention.

Tests of said prototype samples have shown that it is possible to detect modern explosives having a minimal mass of 100 to 150 g in standard luggage of air travelers with a nitrogen density of 2.3 to 2.4 g/dm³, typical of such luggage, in non-explosive nitrogen-containing materials. The probability of correctly detecting a minimal mass of an explosive, experimentally assessed on the basis of test results, has amounted to 0.95–0.97, with the probability of a false alarm not higher than 0.02–0.04.

The system for detecting an explosive in the luggage of air travelers has shown a sufficiently high capacity of luggage checking. The unit for neutron radiation analyses is capable of checking 170–190 pieces of luggage per hour. Taking into consideration that this unit is ordinarily used to check not more than 40% of luggage under inspection suspected to have an explosive during preliminary checking in an X-ray unit with a capacity of 350–370 pieces of luggage per hour and the false alarm probability of about 0.4, the aforementioned capacity of the neutron-radiation analyzing unit can be deemed acceptable even for checking the luggage of a large number of air travelers taken on board of wide-fuselage airliners.

The use of the proposed method increases the probability of correct explosive detection, lowers the probability of a false alarm, diminishes the minimal mass of explosive detectable by the method, shortens the overall time of detecting an explosive, heightens the level of radiation safety, and reduces the probability of deteriorating consumer properties of articles contained in the object under investigation.

What is claimed is:

1. A method for detecting an explosive in an object under investigation, comprising the following steps:
    (a) initially exposing the object under investigation to X-rays for purposes of detecting whether the object contains a nitrogen-containing explosive having an average density range of 1.25 to 2.00 g/cm$^3$;
    (b) recording the X-rays that have passed through the object under investigation;
    (c) finding areas of the object under investigation with a density of organic materials exceeding a pre-established value, on a basis of a value of X-ray attenuation;
    (d) identifying articles contained in the aforementioned found areas of the object under investigation with said density of organic materials higher than the pre-established value, on a basis of an analysis of said recorded X-rays;
    (e) selecting among said areas of the object under investigation an area containing an unidentified article;
    (f) in case all the articles are identified as not containing a nitrogen-containing explosive having an average density range of 1.25 to 2.00 g/cm$^3$ the process of detecting is stopped;
    (g) in case any article is unidentified the method of detecting further comprising:
    (h) determining the dimensions and position of said unidentified article in the object under investigation, on a basis of an analysis of said recorded X-rays;
    (i) evaluating a mass of a nitrogen-containing explosive being detected based on an average density range of 1.25 to 2.00 g/cm$^3$ which corresponds to said dimensions of the unidentified article;
    (k) exposing to thermal neutrons the selected area of the object under investigation containing the unidentified article;
    (l) recording, using at least two gamma-ray detectors, gamma-ray quanta with the energy of 10.8 MeV and pairs of simultaneously emitted cascade gamma-ray quanta emitted by said area of the object under investigation exposed to thermal neutrons;
    (m) counting pairs of said cascade gamma-ray quanta recorded simultaneously;
    (n) determining the overall intensity of gamma rays emitted by the object under investigation;
    (o) determining a threshold value for said overall intensity of gamma rays emitted by the object under investigation, on a basis of said evaluated mass of the explosive being detected which corresponds to the dimensions of the unidentified article;
    (p) making a decision about presence of a nitrogen-containing explosive having an average density range of 1.25 to 2.00 g/cm$^3$ in the object under investigation in the event that said overall intensity of gamma rays emitted by the object under investigation exceeds the said threshold value.

2. A method as set forth in claim 1, wherein said exposure to thermal neutrons of said area of the object under investigation that contains an unidentified article is carried out using a controlled thermal neutron radiator with a variable thermal neutron fluence pattern, which controlled thermal neutron radiator is based on the deuterium-deuterium reaction and is equipped with a neutron moderator.

3. A method as set forth in claim 1, wherein when said recording of the cascade gamma-ray quanta the gamma-ray quanta having the energies of 5.534 MeV and 5.266 MeV are recorded.

4. A method as set forth in claim 1, wherein said determination of overall intensity of gamma rays emitted by the object under investigation is carried out by summing up the numbers of recordings of said 10.8 MeV gamma-ray quanta by each of said gamma-ray detectors multiplied by a weight factor of readings of detector, and the numbers of pairs of said cascade gamma-ray quanta, simultaneously recorded by each of pairs of said gamma-ray detectors, multiplied by weight factor of readings of the pair of detectors.

5. A method as set forth in claim 4, wherein said determination of the weight factor for readings of a pair of detectors is carried out as the arithmetic mean of said weight factors of readings of detectors composing said pair.

6. A method as set forth in claim 1, which includes a reduction of the mass of air surrounding the object under investigation by means other than physical location of said thermal neutron radiator or gamma-ray detectors prior to said exposure to thermal neutrons.

7. A method as set forth in claim 1 which includes a reduction of the mass of air surrounding the object under investigation wherein said reduction of the mass of air surrounding the object under investigation is carried out through air displacement.

8. A method as set forth in claim 7, wherein said exposure to thermal neutrons of said area of the object under investigation that contains an unidentified article is carried out using a controlled thermal neutron radiator with a variable directional pattern, which controlled thermal neutron radiator is based on the deuterium-deuterium reaction and is equipped with a neutron moderator.

9. A method as set forth in claim 7, wherein when said recording of the cascade gamma-ray quanta the gamma-ray quanta having the energies of 5.534 MeV and 5.266 MeV are recorded.

10. A method as set forth in claim 7, wherein said determination of overall intensity of gamma rays emitted by the object under investigation is carried out by summing up the numbers of recordings of said 10.8 MeV gamma-ray quanta by each of said gamma-ray detectors multiplied by a weight factor of readings of detector, and the numbers of pairs of said cascade gamma-ray quanta, simultaneously recorded by each of pairs of said gamma-ray detectors, multiplied by weight factor of readings of the pair of detectors.

11. A method as set forth in claim 10, wherein said determination of the weight factor for readings of a pair of detectors is carried out as the arithmetic mean of said weight factors of readings of detectors composing said pair.

12. A method as set forth in claim 7, wherein said air displacement is carried out with the use of a gaseous medium not containing nitrogen.

* * * * *